(12) United States Patent
Gruber et al.

(10) Patent No.: US 9,574,013 B2
(45) Date of Patent: Feb. 21, 2017

(54) ANTIBODIES AGAINST FACTOR XII AND USES THEREOF

(71) Applicants: VANDERBILT UNIVERSITY, Nashville, TN (US); ARONORA, INC., Portland, OR (US); OREGON HEALTH & SCIENCE UNIVERSITY, Portland, OR (US)

(72) Inventors: Andras Gruber, Portland, OR (US); David Gailani, Nashville, TN (US); Philberta Leung, Portland, OR (US); Anton Matafonov, Nashville, TN (US)

(73) Assignees: VANDERBILT UNIVERSITY, Nashville, TN (US); ARONORA, INC., Portland, OR (US); OREGON HEALTH & SCIENCE UNIVERSITY, Portland, OR (US)

( * ) Notice: Subject to any disclaimer, the term of this patent is extended or adjusted under 35 U.S.C. 154(b) by 64 days.

(21) Appl. No.: 14/649,972

(22) PCT Filed: Dec. 6, 2013

(86) PCT No.: PCT/US2013/073690
§ 371 (c)(1),
(2) Date: Jun. 5, 2015

(87) PCT Pub. No.: WO2014/089493
PCT Pub. Date: Jun. 12, 2014

(65) Prior Publication Data
US 2015/0315292 A1    Nov. 5, 2015

Related U.S. Application Data

(60) Provisional application No. 61/734,630, filed on Dec. 7, 2012.

(51) Int. Cl.
*A61K 39/395* (2006.01)
*C07K 16/36* (2006.01)
*C07K 16/40* (2006.01)
*A61K 39/00* (2006.01)

(52) U.S. Cl.
CPC ............... *C07K 16/40* (2013.01); *C07K 16/36* (2013.01); *A61K 2039/505* (2013.01); *A61K 2039/507* (2013.01); *C07K 2317/33* (2013.01); *C07K 2317/565* (2013.01); *C07K 2317/567* (2013.01); *C07K 2317/76* (2013.01)

(58) Field of Classification Search
None
See application file for complete search history.

(56) References Cited

U.S. PATENT DOCUMENTS 4,963,651 A * 10/1990 Nesheiwat ......... C08G 75/0281
528/388
5,500,349 A * 3/1996 Esnouf .................. C07K 16/40
435/337

8,236,316 B2    8/2012 Gruber et al.
2005/0031614 A1    2/2005 Roskos et al.
2011/0250207 A1   10/2011 Gruber et al.

FOREIGN PATENT DOCUMENTS

| DE | WO 2006066878 A1 * | 6/2006 | ............. A61K 38/55 |
|----|---|---|---|
| GB | WO 2007122371 A1 * | 11/2007 | ............. C07K 16/36 |
| NL | WO 9117258 A1 * | 11/1991 | ............... C07K 7/08 |
| WO | WO 03/013423 | 2/2003 | |
| WO | WO 2005/056604 | 6/2005 | |
| WO | WO 2011/032161 | 3/2011 | |
| WO | WO 2012/112943 | 8/2012 | |
| WO | WO 2012/149412 | 11/2012 | |

OTHER PUBLICATIONS

Muyldermans, S. Annu Rev Biochem. 2013;82:775-97. doi: 10.1146/annurev-biochem-063011-092449. Epub Mar. 13, 2013.*
Campos et al., "Identification and characterization of a novel factor XIIa inhibitor in the hematophagous insect, Triatoma infestans (Hemiptera: Reduviidae)", FEBS Letters, 577: 512-516, 2004.
Cheng et al., "A role for factor XIIa-mediated factor XI activation in thrombus formation in vivo", Blood, 116(19): 3981-3989, 2010.
International Preliminary Report on Patentability issued in International Application No. PCT/US13/73690, mailed Jun. 18, 2015.
International Search Report and Written Opinion issued in International Application No. PCT/US13/73690, mailed Feb. 12, 2014.
Jansen et al., "Inhibition of factor XII in septic baboons attenuates the activation of complement and fibrinolytic systems and reduces the release of interleukin-6 and neutrophil elastase", Blood, 87(6): 2337-44, 1996.
Kleinschnitz et al., "Targeting coagulation factor XII provides protection from pathological thrombosis in cerbral ischemia without interfering with hemostasis", J Exp Med., 2003(3): 513-8, 2006.
Kravlsov et al., "Factor XI contributes to thrombin generation in the absence of factor XII", Blood, 114(2): 452-458, 2009.
Larsson et al., "A factor XIIa inhibitory antibody provides thromboprotection in extracorporeal circulation without increasing bleeding risk", Science Translational Medicine, 6(222): 222ra17, 2014.
Matafonov et al., "Antibodies to human factor XII with antithrontbotic properties", 54th ASH Annual Meeting and Exposition, Abstract 1106, Dec. 8, 2012.
Matafonov et al., "Factor XII inhibition reduces throthbus formation in a primate thrombosis model", Blood, 123(11): 1739-1746, 2014.
Pixley et al., "Activation of the contact system in lethal hypotensive bacteremia in a baboon mode", Am J Pathol., 140(4): 897-906, 1992.
Pixley et al., "The contact system contributes to hypotension but not disseminated intravascular coagulation in lethal bacteremia. In vivo use of a monoclonal anti-factor XII antibody to block contact activation in baboons", J Clin Invest., 91(1): 61-8, 1993.

(Continued)

Primary Examiner — Michael Szperka
(74) Attorney, Agent, or Firm — Parker Highlander, PLLC

(57) ABSTRACT

Provided are antibodies that selectively bind to and inhibit activation of coagulation factor XII. Methods of treatment employing these antibodies are described herein.

20 Claims, 14 Drawing Sheets

(56) References Cited

OTHER PUBLICATIONS

Renné et al., "Defective thrombus formation in mice lacking coagulation factor XII", *J Exp Med.*, 2002(2): 271-81, 2005.
Tucker et al., "Prevention of vascular graft occlusion and thrombus-associated thrombin generation by inhibition of factor XI", *Blood*, 113(4): 936-944, 2009.

* cited by examiner

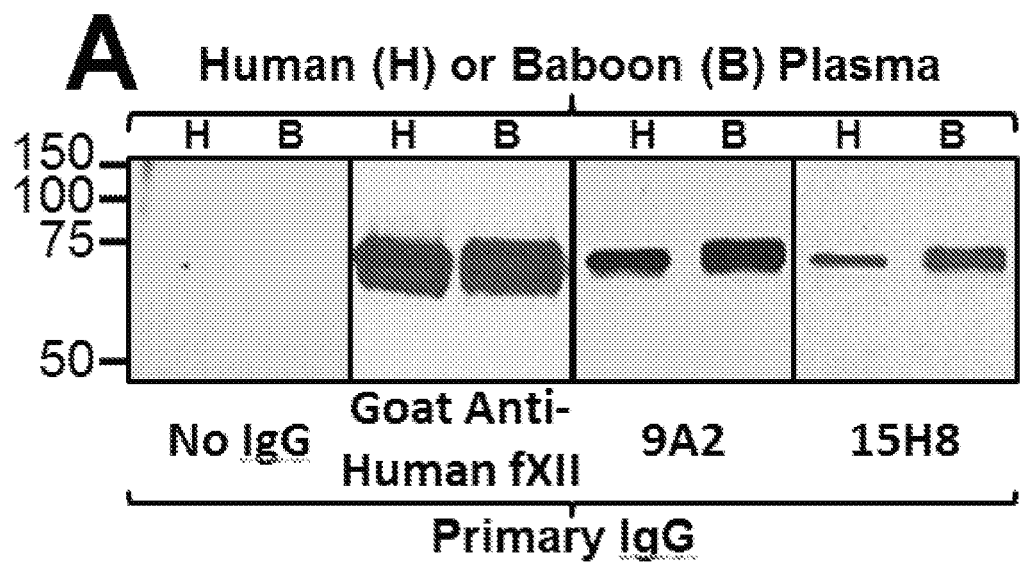
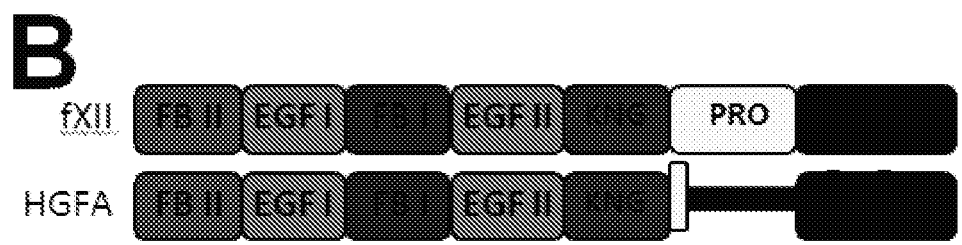
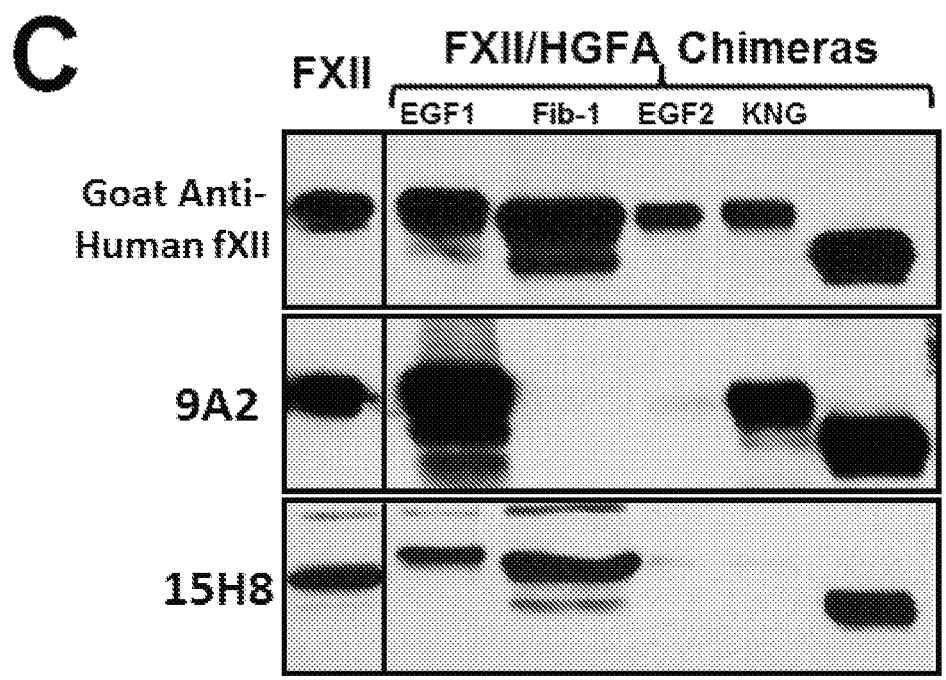
FIGS. 1A-C

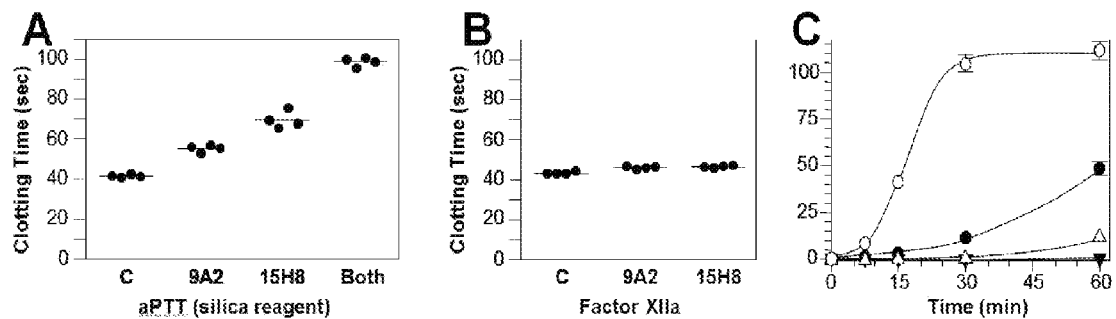
FIGS. 2A-C
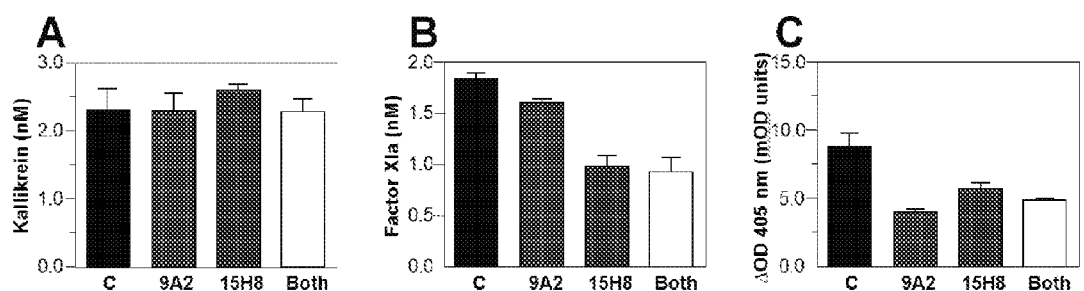
FIGS. 3A-C

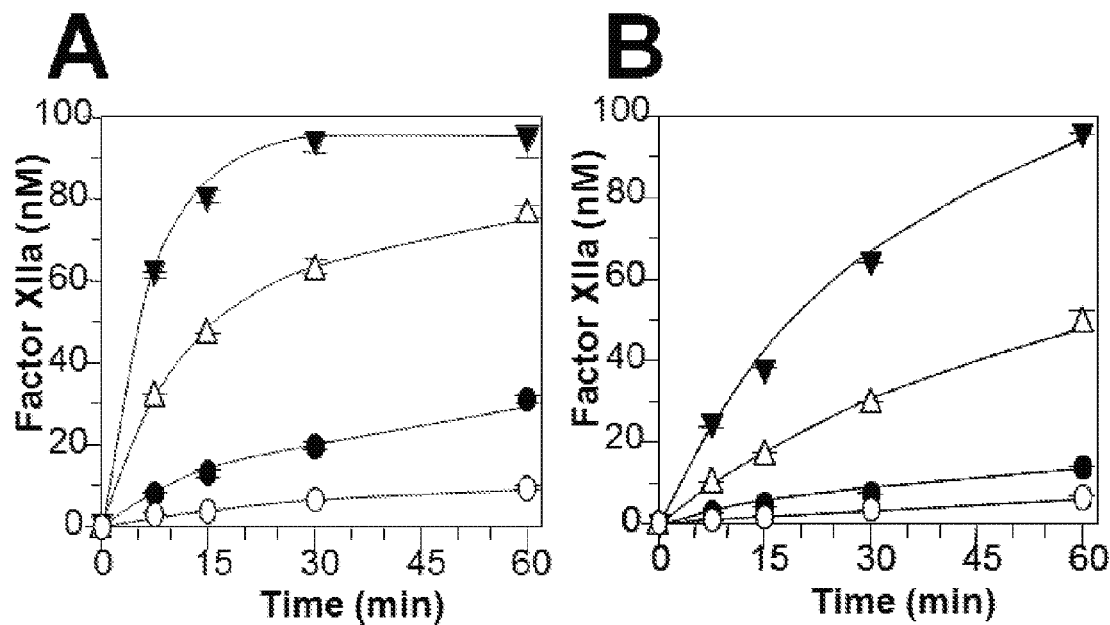
FIGS. 4A-B
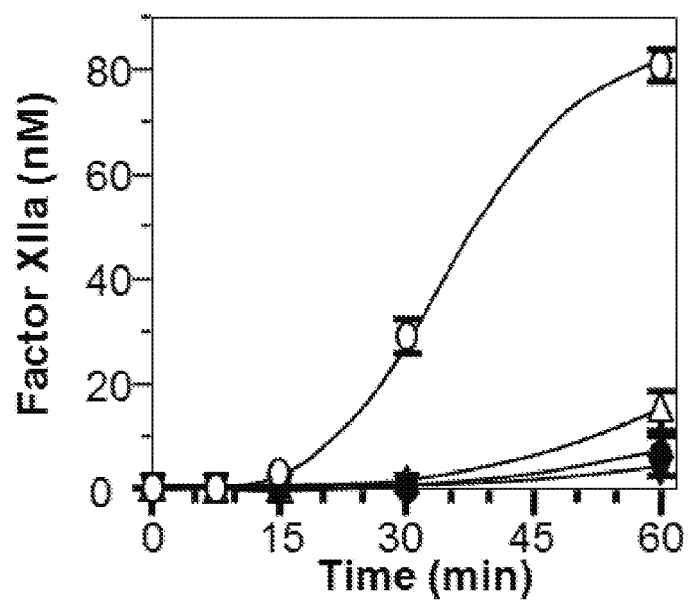
FIG. 5

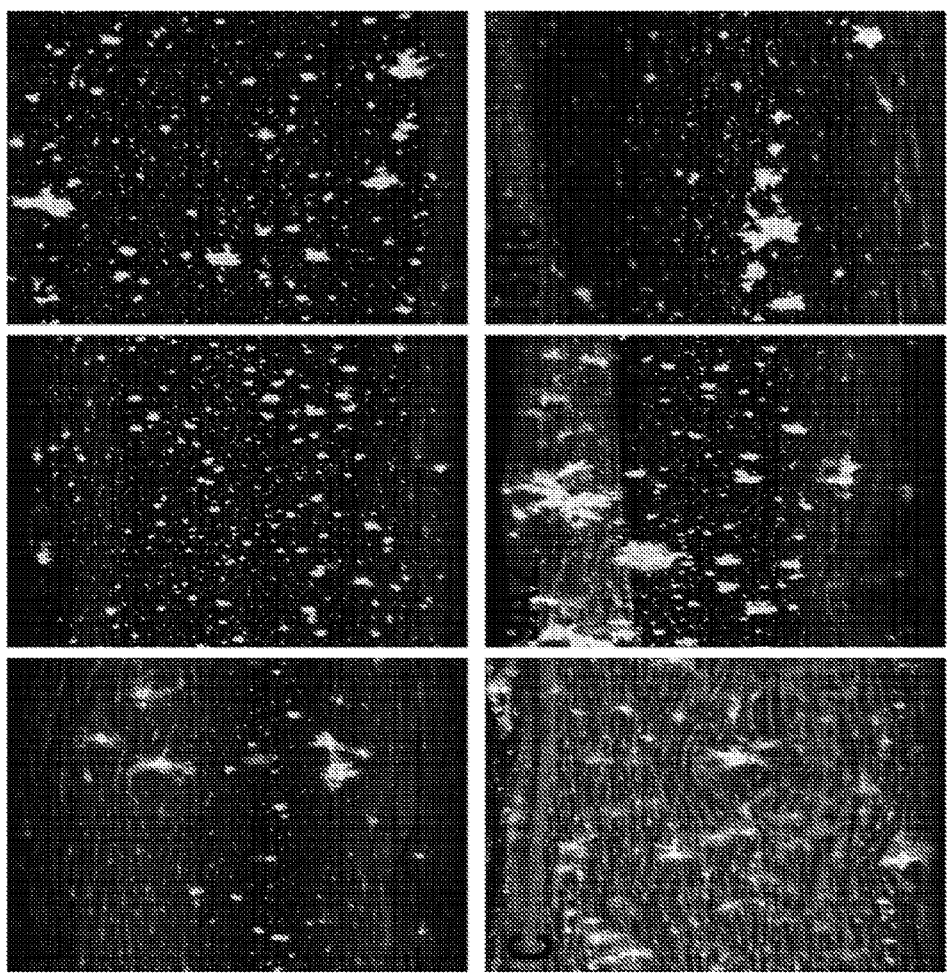
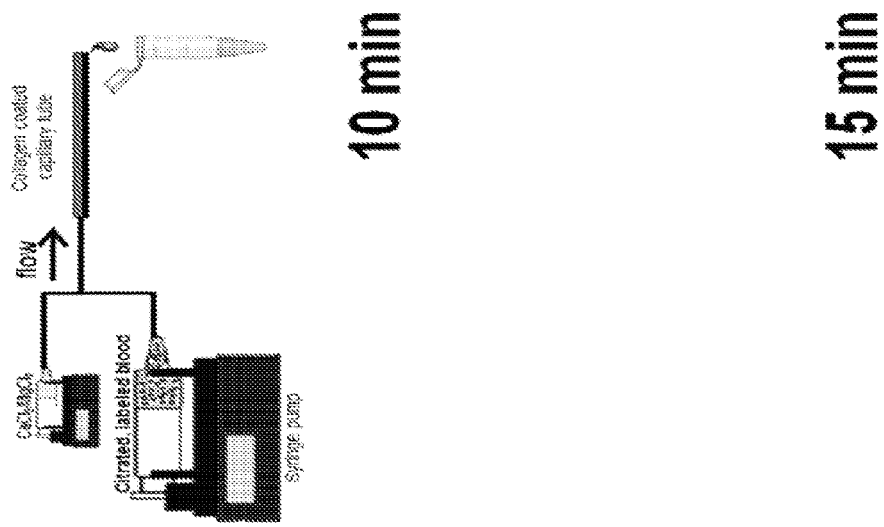
FIG. 8

FIGS. 10A-C

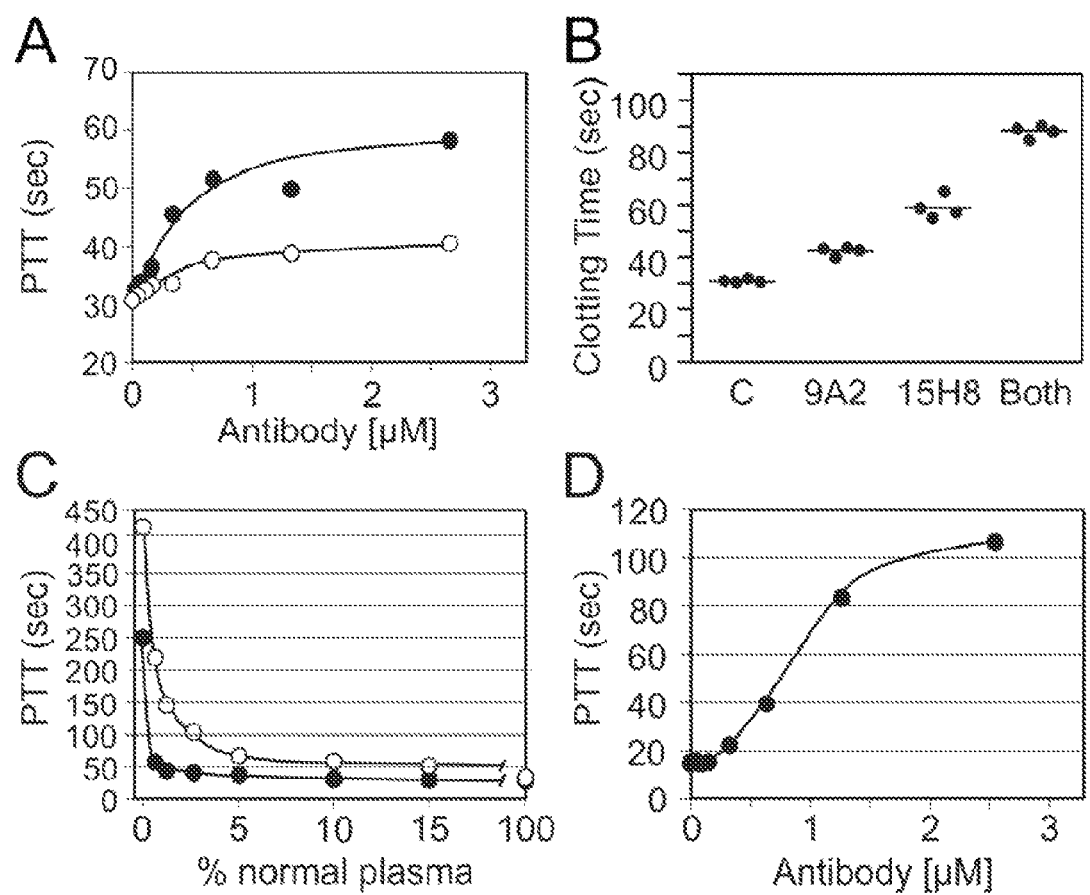
FIGS. 12A-D

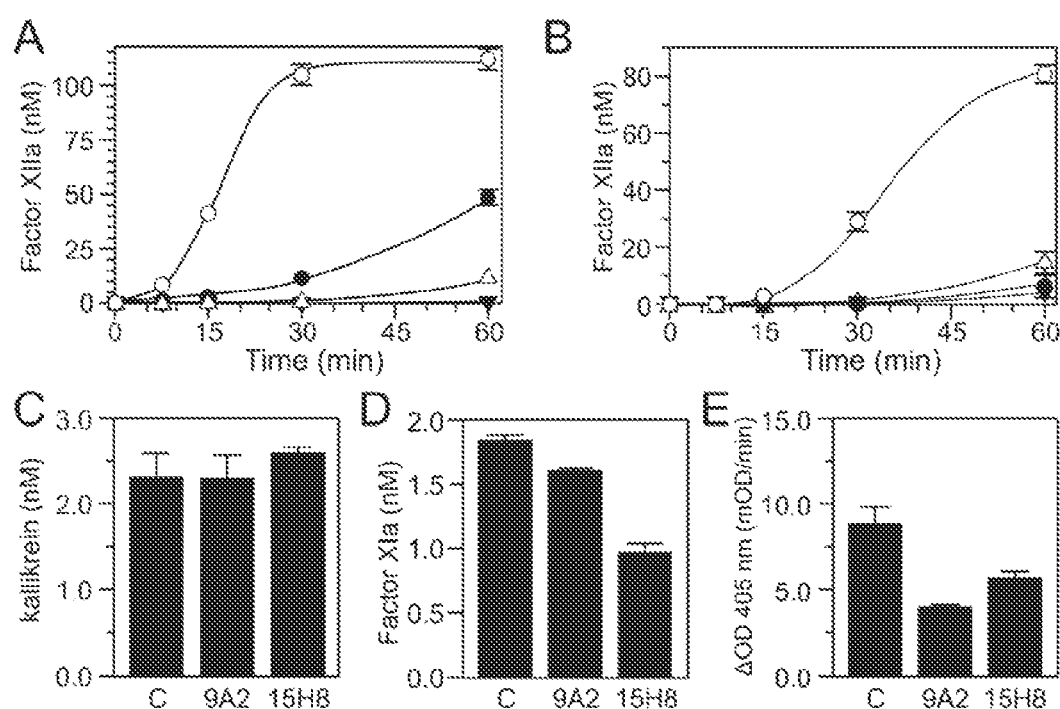
FIGS. 13A-E

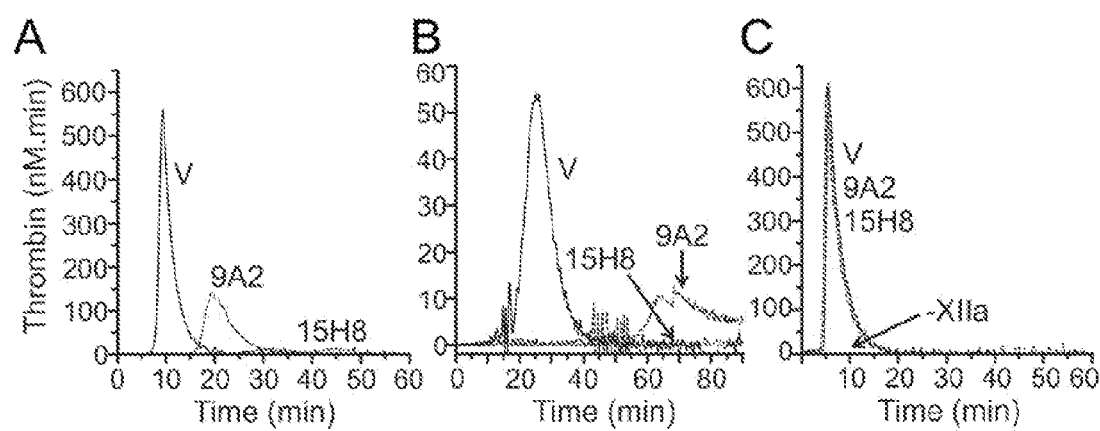
FIGS. 14A-C

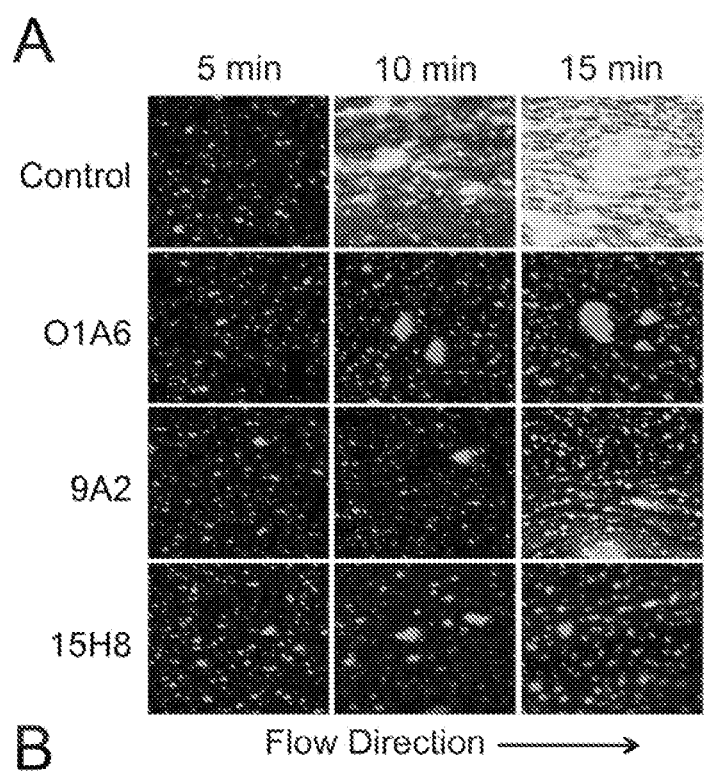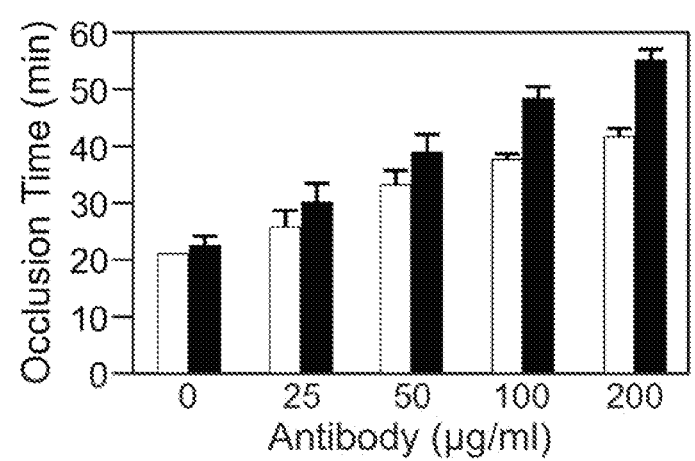
FIGS. 15A-B

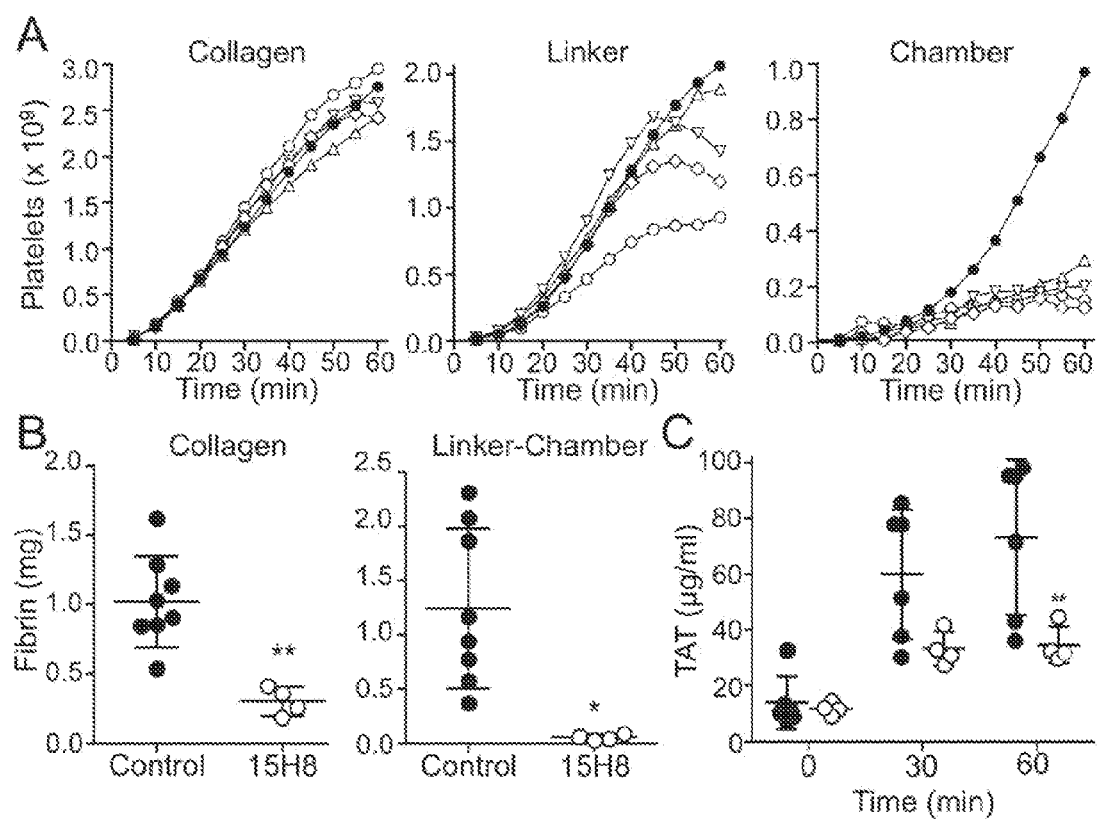
FIGS. 16A-C

ANTIBODIES AGAINST FACTOR XII AND USES THEREOF

PRIORITY INFORMATION

The present application is a national phase application under 35 U.S.C. §371 of International Application No. PCT/US2013/073690, filed Dec. 6, 2013, which claims benefit of priority to U.S. Provisional Application Ser. No. 61/734,630, filed Dec. 7, 2012, the entire contents of each of the above-referenced applications are hereby incorporated by reference.

FEDERAL GRANT SUPPORT

This invention was made with government support under Grant Nos. HL58837 and HL81326 awarded by the National Heart, Lung and Blood Institute, Grant No NS077600 awarded by the National Institute of Neurological Disorders and Stroke, and Grant No AI088937 awarded by the National Institute of Allergy and Infectious Diseases. The government has certain rights in the invention.

BACKGROUND

Blood coagulation is a process consisting of a complex interaction of various blood components, or factors, which eventually give rise to a fibrin clot. Generally, blood components participating in the coagulation "cascade" are proenzymes or zymogens—enzymatically inactive proteins that are converted into an active form by action of an activator. However, when dysregulation of the coagulation cascade occurs, such as due to injury or disease, severe clinical consequences can ensue.

One of these consequences is thrombosis, a general term for diseases caused by the localized accumulation of circulating blood elements within the vasculature that result in vessel occlusion. Conventional antithrombotic drugs can inhibit thrombus growth by targeting coagulation pathways (for example, heparin and warfarin) or platelet-dependent mechanisms (such as aspirin or clopidogrel). Thrombolytic agents (e.g., streptokinase) are used to degrade thrombi in situ to restore blood flow. Despite advances in this field, the search for new strategies continues because existing treatments impair hemostasis, and must be administered at doses that do not achieve maximum efficacy (Gruber and Hanson, 2003).

Hemostasis is a vital function that stops bleeding and protects the integrity of blood circulation on both molecular and macroscopic levels. Hemostasis includes a coagulation cascade of sequentially activatable enzymes that is traditionally divided into three parts: (1) an intrinsic pathway, which includes interactions of blood coagulation proteins that lead to the generation of coagulation factor IXa (fXIa) without involvement of coagulation factor VIIa (fVIIa); (2) an extrinsic pathway, which includes interactions of blood coagulation proteins that lead to the generation of coagulation factor Xa (fXa) and IXa (fIXa) without involvement of factor XI (fXI); and (3) a common coagulation pathway, including interactions of blood coagulation proteins II, V, VIII, IX and X that lead to the generation of thrombin. Thrombin activates platelets and generates fibrin, both of which are essential building elements of the hemostatic plug that is responsible for sealing the vascular breach. Complete absence of thrombin or platelets causes paralysis of hemostasis and leads to lethal hemorrhage.

The plasmas of placental and marsupial mammals contain fXI (Ponczek et al., 2008), the zymogen of a plasma protease (fXIa) that contributes to fibrin formation and stability through fIX activation (Furie et al., 2005). fXI deficiency causes a variable trauma-induced hemorrhagic disorder in humans and other species (Seligsohn et al., 2007; Knowler et al., 1994; Ghanem et al., 2005; Troxel et al., 2002). The physiologic mechanism by which fXI is converted to fXIa has been a topic of debate (Pedicord et al., 2007; Blat & Seiffert, 2008). When blood is exposed to a charged surface, the process of contact activation converts factor XII (fXII) to the protease fXIIa, which then activates fXI (Gailani and Broze, 2001). This reaction does not contribute to hemostasis as fXII deficiency, unlike fXI deficiency, is not associated with abnormal bleeding in any species in which it has been identified (Gailani and Broze, 2001). This is a key piece of supporting evidence for hypotheses proposing that fXI is either activated during hemostasis by a protease distinct from fXIIa, or that auxiliary mechanisms for fXI activation can compensate for the absence of fXIIa (Broze et al., 1990; Davie et al., 1991; Renne et al., 2007).

In addition to fXIIa, other candidates for fXI activators include α-thrombin (Naito et al., 1991; Gailani et al., 1991), meizothrombin (von dem Borne et al., 1997), and fXIa (autoactivation) (Naito et al., 1991; Gailani et al., 1991). Thrombin has received much attention in this regard. Work from several laboratories supports a model in which thrombin or another protease generated early in coagulation activates fXI (von dem Borne et al., 1997; von dem Borne et al., 1995; von dem Borne et al., 1997; Cawthern et al., 1998; Keularts et al., 2001; Oliver et al., 1999; Wielders et al., 2004), with fXIa then sustaining coagulation. This hypothesis has been challenged by a study that did not find evidence for fXI activation in thrombin or tissue factor (TF) stimulated plasma in the absence of fXII (Pedicord et al., 2007). This work also showed that the process of collecting and preparing plasma can generate fXIa, giving the false impression in subsequent assays that fXIIa-independent fXI activation has occurred. These observations have been presented in support of a hypothesis, proposed previously by other investigators (Brunnee et al., 1993), that normal hemostasis in fXII deficiency reflects loss of fXIIa-initiated processes, such as fibrinolysis, that negate the propensity to bleed from simultaneous loss of fXI activation (Pedicord et al., 2007; Blat et al., 2008).

Coagulation fXII has long been considered a potential therapeutic target in some disease conditions where contact activation may contribute to pathogenesis. However, no sufficiently potent inhibitor for fXII activity, such as a potent and useful antibody, has yet been identified. Antibodies to fXII exist, but these apparently lack the potency and properties necessary for an effective therapeutic (Pixley et al., 1993). Thus, a need exists for a potent and specific inhibitor of fXII.

SUMMARY

Thus, there is provided an antibody comprising (a) a light chain comprising light chain CDRs represented by SEQ ID NOS: 1, 2 and 3; and (b) a heavy chain comprising heavy chain CDRs represented by SEQ ID NOS: 4, 5 and 6. The antibody maybe a humanized antibody, and may have the following sequence composition:

TABLE 1

Antibody Sequences

|  | LDR | FR$_1$ | CDR1 | FR$_2$ | CDR2 | FR$_3$ | CDR3 | FR$_4$ |
|---|---|---|---|---|---|---|---|---|
| Light Chain CDR | | | | | | | | |
| SEQ ID NO: | | | 1 | | 2 | | 3 | |
| Heavy Chain CDR | | | | | | | | |
| SEQ ID NO: | | | 4 | | 5 | | 6 | |
| Light Chain Framework | | | | | | | | |
| SEQ ID NO: | | 7 | | 8 | | 9 | | 10 |
| Heavy Chain Framework | | | | | | | | |
| SEQ ID NO: | | 11 | | 12 | | 13 | | 14 |
| Light Chain Leader | | | | | | | | |
| SEQ ID NO: | 16 | | | | | | | |
| Heavy Chain Leader | | | | | | | | |
| SEQ ID NO: | 18 | | | | | | | |

The antibody may have light chain framework regions represented by SEQ ID NOS: 7, 8, 9 and 10, or having 5 or fewer conservative amino acid substitutions. The antibody may have heavy chain framework regions represented by SEQ ID NOS: 11, 12, 13 and 14, or having 5 or fewer conservative amino acid substitutions. The light chain may be represented by SEQ ID NO: 15. The light chain leader sequence may be represented by SEQ ID NO: 16. The light chain may be encoded by a nucleic acid represented by SEQ ID NO: 19. The heavy chain may be represented by SEQ ID NO: 17. The heavy chain leader sequence may be represented by SEQ ID NO: 18. The heavy chain may be encoded by a nucleic acid represented by SEQ ID NO: 20. The antibody may be a single-chain or single-domain antibody, or an antibody fragment, such as Fab', Fab, F(ab')$_2$, a single domain antibody, Fv, scFv, or bivalent antibody. Also provided is a cell or cell line comprising a nucleic acid encoding an antibody as described above. Also provide is a pharmaceutical composition comprising an antibody as described above, dispersed in a pharmaceutically acceptable carrier.

In other embodiment, there are provided methods of using the antibodies or pharmaceutical compositions described above, such as:
- a method of inhibiting activation of factor XII comprising contacting unactivated factor XII with an antibody as described above;
- a method of inhibiting activation of Factor XII in a subject comprising administering an effective amount of an antibody as described above;
- a method of treating pathologic hypercoagulation involving activation of factor XII in a subject comprising administering an effective amount of an antibody as described above;
- a method of preventing pathologic hypergcoagulation involving activation of factor XII in a subject comprising administrating an effective amount of an antibody as described above; or
- a method of modulating thrombosis involving activation of factor XII in a subject comprising administrating an effective amount of an antibody as described above.

The methods may involve a subject suffers from or is at risk of a bacterial infection, a fungal infection, a viral infection, a parasite infection, an ischemic organ disease, microvascular thrombosis, macrovascular thrombosis, thromboembolism (e.g., pulmonary), disseminated intravascular coagulation, severe systemic inflammatory response syndrome, acute respiratory distress syndrome, cancer, amniotic fluid embolism, trauma, transplant rejection, sickle cell disease, or medical device implantation. Ischemic organ disease may be myocardial infarction or ischemic stroke. Cancer may be non-metastatic solid tumor cancer, metastatic solid tumor cancer or leukemia. The medical device implantation may be implantation of a catheter, heart valve, stent or graft. The method may further comprise administering to said subject a second anti-coagulant therapy, or an antithrombotic or thrombolytic therapy. The antibody may be administered is sufficient to inhibit activation of Factor XII by about 50%, about 75%, about 90% or about 95%. The antibody may be administered to the subject by parenteral administration. The antibody may be administered at a dose of about 0.1 mg/kg to about 20 mg/kg. The subject may be dosed with the antibody more than once, such as chronically.

In yet another embodiment, there is provide a n isolated nucleic acid encoding an antibody comprising (a) a light chain comprising light chain CDRs represented by SEQ ID NOS: 1, 2 and 3; and (b) a heavy chain comprising heavy chain CDRs represented by SEQ ID NOS: 4, 5 and 6. Also provided is an expression vector comprising a nucleic acid encoding the same, wherein said nucleic acid is under the operational control of a promoter.

Yet a further embodiment comprises a kit comprising containing an antibody or cell as described above. The antibody may be labeled. The kit may further comprise a buffer or diluent, and or further comprises instructions on the use of said antibody or cell. The antibody is present in an aqueous suspension or lyophilized.

It is contemplated that any embodiment discussed in this specification can be implemented with respect to any compound, method, or composition, and vice versa.

Other objects, features and advantages will become apparent from the following detailed description. It should be understood, however, that the detailed description and the specific examples, while indicating specific embodiments, are given by way of illustration only, since various changes and modifications within the spirit and scope will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-C. Mapping AB042 and AB043 binding sites. (FIG. 1A) Western blots of human (H) and baboon (B) plasma size fractionated by SDS-PAGE. Primary antibodies are indicated below each panel. (FIG. 1B) Schematic diagrams comparing the domain structures of fXII and its homolog hepatocyte growth factor activator (HGFA). (FIG. 1C) Western blots of the wild-type human fXII (left lane) and human fXII with the indicated domains replaced with the corresponding domains from HGFA. A chimera for the N-terminal fibronectin type II domain could not be expressed. Primary antibodies are goat-polyclonal anti-human fXII (top panel), monoclonal anti-human fXII AB043 (middle panel), and monoclonal anti-human fXII AB042 (bottom panel).

FIGS. 2A-C. AB043 and AB042 interfere with fXII activation. (FIG. 2A) Effect of monoclonal antibodies in human plasma at concentrations of 4 µM (10× the plasma fXII concentration) in a standard aPTT assay using a silica-based PTT reagent. Each circle represents a single clotting time, and the bar indicates the mean for the group. (FIG. 2B) FXIIa (50 nM) was incubated with antibody (1 µM) or vehicle for 15 minutes prior to adding it to plasma. FXIIa was measured by a chromogenic substrate cleavage assay (S-2302). (FIG. 2C) Time course of fXII (100 nM) activation with PTT reagent (2.5% of total volume) at 37° C. in the presence of 1 µM AB043 (●), AB042 (Δ), AB043+ AB042AB043 (▼) or vehicle (○).

FIGS. 3A-C. AB043 and AB042 effect on prekallikrein (PK) and FXI activation by fXIIa. (FIG. 3A) PK (50 nM) was incubated with fXIIa (1 nM) in the presence of 10 nM antibodies or vehicle for 15 minutes at 37° C. The fXIIa was incubated at a higher concentration with a 10-fold excess of antibody before dilution to run the assay. (FIG. 3B) FXI (100 nM) was incubated with fXIIa (30 nM) for 1 hour at 37° C. in the presence of 300 nM antibody or vehicle. After incubation, corn trypsin inhibitor was added to inhibit fXIIa, and fXIa was measured by chromogenic substrate cleavage (S-2366). (FIG. 3C) Reciprocal activation of PK and fXII. PK (150 nM) and FXII (100 nM) were incubated at 37° C. for 15 minutes with or without 1 µM antibody.

FIGS. 4A-B. AB043 and AB042 enhance fXII activation by fXIa and kallikrein. Time course of fXII (100 nM) activation by 25 nM (FIG. 4A) fXIa or (FIG. 4B) kallikrein at 37° C. in the absence or presence of 1 µM antibody. Reactions were stopped by addition of soybean trypsin inhibitor and fXIIa was measured by chromogenic substrate cleavage (S-2302). Symbols are (○) vehicle, (●) AB043, (Δ) AB042, and (▼) AB043+AB042.

FIG. 5. Effects of AB043 and AB042 on polyphosphate-induced fXII activation. FXII (100 nM) was incubated with 2 µM polyphosphate for 1 hr at 37° C. Reaction was stopped with Polybrene and fXIIa activity was measured by cleavage of chromogenic substrate (S-2302). Symbols are (○) vehicle, (●) AB043, (Δ) AB042, and (▼) AB043+AB042.

FIG. 8. Human ex vivo blood flow model. Recalcified human whole blood was perfused through collagen-coated capillary tubes (0.2×2×50 mm) at a shear rate of 300 s$^{-1}$ s for 10 (top) or 15 (bottom) minutes at 37° C. Blood was incubated with vehicle (C) or 4 µM AB043 or AB042 IgG for 30 minutes prior the experiment. Blood contains fluorescently labeled fibrinogen and platelets. After perfusion, tubes was washed, fixed and imaged by fluorescent microscopy. Fibrin is red and platelets are green.

(FIG. 10A) Schematic diagrams comparing the domain structures of fXII and its homolog hepatocyte growth factor activator (HGFA). Arrowed numbers indicate the locations of amino acid pairs that were used to create splice sites for introduction of HGFA domains into fXII to create fXII/HGFA chimeras. (FIG. 10B) Western blots of human (H) and baboon (B) plasma size-fractionated by SDS-PAGE. The primary anti-factor XII antibodies used for detection are indicated at the top of each panel. (FIG. 10C) Western blots of wild type human fXII (FXII) and human fXII with the first or second epidermal growth factor (EGF1 or EGF2), fibronectin type 1 (Fib-1), kringle (KNG) or proline rich (ProR) domains replaced with the corresponding HGFA domain. Primary antibodies are indicated to the left of each blot. Poly—Polyclonal goat IgG against human factor XII.

FIGS. 12A-D. Effects of anti-factor XII antibodies on plasma coagulation. (FIG. 12A) Results of a standard aPTT assay using a silica-based reagent for normal plasma supplemented with different concentrations of IgG 9A2 (○) or 15H8 (●). Data are averages of two clotting times. (FIG. 12B) aPTT assay of normal plasma supplemented with control vehicle (C), 4 µM 9A2 or 15H8, or 4 µM of both antibodies. Each circle represents a single clotting time, and the bar indicates the mean for the group. (FIG. 12C) aPTT results for human factor XII deficient plasma mixed with normal human (○) or baboon (●) plasma in various ratios. (FIG. 12D) Effect of different concentrations of IgG 15H8 on the PTT of baboon plasma.

FIGS. 13A-E. Effects of anti-factor XII antibodies on factor XII activation and factor XIIa activity. (FIGS. 13A-B) Conversion of fXII to fXIIa in the presence of (FIG. 13A) a silica-based PTT reagent or (FIG. 13B) polyphosphate and vehicle (○), 9A2 (●), 15H8 (∆), or the combination of 9A2 and 15H8 (▼). (FIG. 13C) FXIIa (100 nM) was incubated with vehicle control (C) or antibody (1 µM) for 15 minutes at 37° C., prior to diluting to 1 nM final concentration. PK was added (50 nM final concentration), followed by incubation at 37° C. for 15 minutes. Reactions were terminated with an excess of corn trypsin inhibitor and the amount of α-kallikrein generated was determined with a chromogenic substrate assay. (FIG. 13D) Same as in FIG. 13C except that fXIIa was at 30 nM final concentration, and fXI (100 nM) replaced PK. FXIa generated was detected with a chromogenic substrate assay. (FIG. 13) PK (150 nM) and FXII (100 nM) were incubated at 37° C. for 15 minutes with or without 1 µM antibody. Reciprocal activation of the two proteins was detected by cleavage of the chromogenic substrate S-2303, which reflects generation of a combination of fXIIa and α-kallikrein.

FIGS. 14A-C. Effects of anti-factor XII antibodies on thrombin generation. Shown are the effects of 4 µM 9A2 and 15H8 or vehicle (V) on thrombin generation in normal plasma triggered with PTT-A reagent (FIG. 14A) or collagen (FIG. 14B). No thrombin is generated in the absence of PTT-A reagent or collagen. (FIG. 14C) Thrombin generation in fXII-deficient plasma supplemented with 5 nM fXIIa in the presence of 500 nM 9A2, 15H8 or vehicle (V). XIIa indicates that no thrombin was generated in the absence of fXIIa.

FIGS. 15A-B. Effect of anti-IXII antibodies on fibrin formation in human blood under flow. (FIG. 15A) Immunofluorescent images (Zeiss LSM 710, objective lenses: 20×/0.80 plan-apochromat, 20× magnification) showing the effects of the anti-fXI IgG O1A6 (300 nM) or the anti-fXII IgGs 9A2 and 15H8 (4 µM) on fibrin deposition over time in recalcified human blood flowing across collagen coated surfaces with an initial average shear rate of 300 sec$^{-1}$. Direction of flow is indicated at the bottom of the image. Fibrin appears orange in these images and platelet aggregates appear green. (FIG. 15B) Collagen-coated glass capillary tubes were perfused with recalcified human blood driven by a constant pressure gradient under the force of gravity. Shown are times to capillary occlusion in the presence of varying concentrations of 9A2 (white bars) or 15H8 (black bars). Each bar represents means for three separate measurements±SE.

FIGS. 16A-C. Effect of 15H8 on platelet and fibrin deposition in a baboon arteriovenous shunt thrombosis model. Thrombogenic devices depicted in FIG. 11 were inserted into femoral arteriovenous shunts in olive baboons as described.[9,13,14] Flow through the grafts was maintained at 100 ml/min, producing an initial average wall shear rate of 265 s$^{-1}$ within the 4 mm diameter portions of the graft. (FIG. 16A) Platelet accumulation in the collagen-coated, silicon linker, and silicon expansion chamber segments of grafts was assessed in real-time by imaging of local 111In-labeled platelet accumulation using a GE-400T camera with NuQuest InteCam. The curves comprised of closed circles (●) represent mean values for nine devices inserted into AV shunts in two untreated animals (control results). Individual results for four devices tested in the same two animals at least one hour after administration of anti-fXII antibody 15H8 (5-6 mg/kg IV) are indicated by the symbols ○, ∆, ▽ and ◊. (FIG. 16B) Results of end-point determinations of total $^{125}$I-labeled fibrin deposition during the experiments in panel A. Fibrin deposition in the collagen-coated graft segment (left panel) and in the silicon expansion chamber (right panel) were determined for 8 of the 9 devices inserted before animals received 15H8 (●) and the 4 devices tested after animals received 15H8 (○). Large bars indicate mean values and smaller bars±1 SD. Results for grafts placed post-15H8 administration are significantly different (p<0.5) for both the collagen coated (**) and linker-chamber (*) graft segments (Student T-test). (C) Plasma thrombin-antithrombin (TAT) complex measured in blood obtained at various times after graft insertion from the arteriovenous shunt upstream of the site of graft insertion for 6 of 8 control grafts (●), and the four grafts placed after 15H8 administration (○). Large bars indicate mean values and smaller bars±1 SD. Results for grafts placed post-15H8 administration are significantly different (p<0.5) at 60 minutes (**) from grafts placed before 15H8 administration. (2-way ANOVA).

DETAILED DESCRIPTION

I. Definitions

Figure 6:
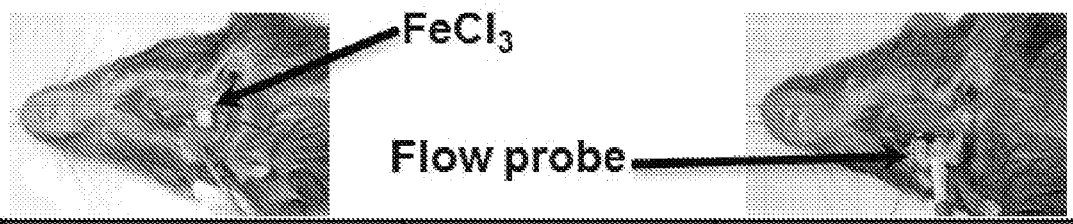
FIG. 6. Effect of AB043 and AB042 on arterial thrombosis in mice. C57Bl/6fXII deficient mice are resistant to carotid artery occlusion induced by 3.5% FeCl$_3$. Human fXII (10 µg) was infused into these mice to produce a plasma level ~30% of that found in humans. Mice supplemented with human fXII then received anti-human fXII IgG (100 µg) 15 minutes prior to FeCl$_3$ injury.

Whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and are not limiting. For example, the term "including" shall mean "including, but not limited to."

The term "factor XII" or "fXII" as used herein refers to any variant, isoform, and/or species homolog of fXII that is naturally expressed by cells and present in plasma.

As used herein, an "antibody" refers to a whole antibody and any antigen binding fragment (i.e., "antigen-binding portion") or single chain thereof. The term includes a full-length immunoglobulin molecule (e.g., an IgG antibody) that is naturally occurring or formed by normal immunoglobulin gene fragment recombinatorial processes, or an immunologically active portion of an immunoglobulin molecule, such as an antibody fragment, that retains the specific binding activity. Regardless of structure, an antibody fragment binds with the same antigen that is recognized by the full-length antibody. For example, an anti-fXII monoclonal antibody fragment binds to an epitope of fXII. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., 1989), which consists of a $V_H$ domain; (vi) an isolated complementarity determining region (CDR); (vii) minibodies, diaboidies, triabodies, tetrabodies, and kappa bodies (see, e.g., Ill et al., 1997); (viii) camel IgG; and (ix) IgNAR. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988; Huston et al., 1988). Such single chain antibodies are also intended to be encompassed within the term "antigen-binding portion" of an antibody. These antibody fragments are obtained using conventional techniques known to those with skill in the art, and the fragments are analyzed for utility in the same manner as are intact antibodies.

Furthermore, it is contemplated that an antigen binding fragment can be encompassed in an antibody mimetic. The term "antibody mimetic" or "mimetic" as used herein is meant a protein that exhibits binding similar to an antibody but is a smaller alternative antibody or a non-antibody protein. Such antibody mimetic can be comprised in a scaffold. The term "scaffold" refers to a polypeptide platform for the engineering of new products with tailored functions and characteristics.

As used herein, the term "anti-fXII antibody" refers to an antibody that specifically binds to an epitope of fXII. When bound in vivo to an epitope of fXII, the anti-fXII antibodies disclosed herein augment one or more aspects of the blood clotting cascade.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity that have variable and constant regions derived from human germline immunoglobulin sequences. The human antibodies can include amino acid residues not encoded by human germline immunoglobulin sequences (e.g., mutations introduced by random or site-specific mutagenesis in vitro or by somatic mutation in vivo).

An "isolated antibody," as used herein, is intended to refer to an antibody which is substantially free of other biological molecules, including antibodies having different antigenic specificities (e.g., an isolated antibody that binds to fXII is substantially free of antibodies that bind antigens other than fXII). In some embodiments, the isolated antibody is at least about 75%, about 80%, about 90%, about 95%, about 97%, about 99%, about 99.9% or about 100% pure by dry weight. In some embodiments, purity can be measured by a method such as column chromatography, polyacrylamide gel electrophoresis, or HPLC analysis. An isolated antibody that binds to an epitope, isoform or variant of human fXII can, however, have cross-reactivity to other related antigens, e.g., from other species (e.g., fXII species homologs). Moreover, an isolated antibody can be substantially free of other cellular material and/or chemicals. As used herein, "specific binding" refers to antibody binding to a predetermined antigen. Typically, an antibody that exhibits "specific binding" binds to an antigen with an affinity of at least about $10^5$ $M^{-1}$ and binds to that antigen with an affinity that is higher, for example at least two-fold greater, than its binding affinity for an irrelevant antigen (e.g., BSA, casein). The phrases "an antibody recognizing an antigen" and "an antibody specific for an antigen" are used interchangeably herein with the term "an antibody which binds specifically to an antigen."

As used herein, the term "minimal binding" refers to an antibody that does not bind to and/or exhibits low affinity to a specified antigen. Typically, an antibody having minimal binding to an antigen binds to that antigen with an affinity that is lower than about $10^2$ $M^{-1}$ and does not bind to a predetermined antigen with higher affinity than it binds to an irrelevant antigen.

As used herein, the term "high affinity" for an antibody, such as an IgG antibody refers to a binding affinity of at least about $10^7 M^{-1}$, in at least one embodiment at least about $10^8 M^{-1}$, in some embodiments at least about $10^9 M^{-1}$, $10^{10} M^{-1}$, $10^{11} M^{-1}$ or greater, e.g., up to $10^{13} M^{-1}$ or greater. However, "high affinity" binding can vary for other antibody isotypes. For example, "high affinity" binding for an IgM isotype refers to a binding affinity of at least about $10^7 M^{-1}$. As used herein, "isotype" refers to the antibody class (e.g., IgM or IgG1) that is encoded by heavy chain constant region genes.

"Complementarity-determining region" or "CDR" refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1," "CDR2," and "CDR3," respectively (Wu et al. 1975; Wu and Kabat, 1970). CDRs are involved in antigen-antibody binding, and the CDR3 comprises a unique region specific for antigen-antibody binding. An antigen-binding site, therefore, can include six CDRs, comprising the CDR regions from each of a heavy and a light chain V region.

The term "epitope" refers to the area or region of an antigen to which an antibody specifically binds or interacts, which in some embodiments indicates where the antigen is in physical contact with the antibody. Conversely, the term "paratope" refers to the area or region of the antibody on which the antigen specifically binds. Epitopes characterized by competition binding are said to be overlapping if the binding of the corresponding antibodies are mutually exclusive, i.e., binding of one antibody excludes simultaneous binding of another antibody. The epitopes are said to be separate (unique) if the antigen is able to accommodate binding of both corresponding antibodies simultaneously.

The term "competing antibodies," as used herein, refers to antibodies that bind to about, substantially or essentially the same, or even the same, epitope as an antibody against fXII as described herein. "Competing antibodies" include antibodies with overlapping epitope specificities. Competing antibodies are thus able to effectively compete with an antibody as described herein for binding to fXII. In some embodiments, the competing antibody can bind to the same epitope as the antibody described herein. Alternatively viewed, the competing antibody has the same epitope specificity as the antibody described herein.

"Coagulation" is the process of polymerization of fibrin monomers, resulting in the transformation of blood or plasma from a liquid to a gel phase. Coagulation of liquid blood may occur in vitro, intravascularly or at an exposed and injured tissue surface. In vitro blood coagulation results in a gelled blood that maintains the cellular and other blood components in essentially the same relative proportions as found in non-coagulated blood, except for a reduction in fibrinogen content and a corresponding increase in fibrin.

"Therapeutically effective amount" is a quantity of a specific substance sufficient to achieve a desired effect in a subject being treated. For instance, this can be the amount necessary to inhibit activation of fXI. When administered to a subject, a dosage will generally be used that will achieve target tissue concentrations that has been shown to achieve a desired in vitro effect.

"Thrombosis" is the formation or presence of a clot (also called a "thrombus") inside a blood vessel, obstructing the flow of blood through the circulatory system. Thrombosis is usually caused by abnormalities in the composition of the blood, quality of the vessel wall and/or nature of the blood flow. The formation of a clot is often caused by an injury to the vessel wall (such as from trauma or infection) and by the slowing or stagnation of blood flow past the point of injury. In some cases, abnormalities in coagulation cause thrombosis.

As used herein, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine), and aromatic side chains (e.g., tyrosine, phenylalanine, tryptophan, histidine). Antibodies of the present disclosure can have one or more conservative amino acid substitutions yet retain antigen binding activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, in some embodiments about 90%, 91%, 92%, 93%, 94%, or 95%, in at least one embodiment at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. Also included are nucleic acid sequences and polypeptide sequences having substantial homology to the specific nucleic acid sequences and amino acid sequences recited herein.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40. (further details found at the world-wide-web at invitrogen.com/site/us/en/home/LINNEA-Online-Guides/LINNEA-CommunitiesNector-NTI-Community/Sequence-analysis-and-data-management-software-for-PCs/AlignX-Module-for-Vector-NTI-Advance.reg.us.html).

Another method for determining the best overall match between a query sequence (a sequence of the present disclosure) and a subject sequence, also referred to as a global sequence alignment, can be determined using the CLUSTALW computer program (Thompson et al., 1994), which is based on the algorithm of Higgins et al., 1992). In a sequence alignment the query and subject sequences are both DNA sequences. The result of said global sequence alignment is in percent identity. Parameters that can be used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty=0.1. For multiple alignments, the following CLUSTALW parameters can be used: Gap Opening Penalty=10, Gap Extension Parameter=0.05; Gap Separation Penalty Range=8; % Identity for Alignment Delay=40.

The nucleic acids can be present in whole cells, in a cell lysate, or in a partially purified or substantially pure form. A nucleic acid is "isolated" or "rendered substantially pure" when purified away from other cellular components with which it is normally associated in the natural environment. To isolate a nucleic acid, standard techniques such as the following can be used: alkaline/SDS treatment, CsCl banding, column chromatography, agarose gel electrophoresis and others well known in the art.

II. Factor XII

FXII is a serum glycoprotein that participates in the initiation of blood coagulation, fibrinolysis, and the generation of bradykinin and angiotensin. Prekallikrein is cleaved by factor XII to form kallikrein, which then cleaves fXII first to α-fXIIa, and then trypsin cleaves it to beta-fXIIa. α-fXIIa activates fXI to fXIa. It also drives selective cleavage of Arg-|-Ile bonds in fVII to form fVIIa and fXI to form fXIa. FXII interacts with HRG; the interaction, which is enhanced in the presence of zinc ions and inhibited by heparin-binding, inhibits fXII autoactivation and contact-initiated coagulation.

Factor XII is activated by kallikrein in α-fXIIa, which is then further converted by trypsin into beta-fXIIa. α-fXIIa is composed of the NH2-terminal heavy chain (Coagulation factor XIIa heavy chain) and the COOH-terminal light chain (coagulation fXIIa light chain), connected by a disulfide bond. Beta-fXIIa is composed of 2 chains linked by a disulfide bond, a light chain (beta-fXIIa part 2), corresponding to the COOH-terminal light chain (Coagulation fXIIa light chain) and a nonapeptide (beta-fXIIa part 1).

Defects in fXII are the cause of fXII deficiency (FA12D), also known as Hageman factor deficiency. This trait is an asymptomatic anomaly of in vitro blood coagulation. Its diagnosis is based on finding a low plasma activity of the factor in coagulating assays. It is usually only accidentally discovered through pre-operative blood tests. FXII deficiency is divided into two categories, a cross-reacting material (CRM)-negative group (negative fXII antigen detection) and a CRM-positive group (positive fXII antigen detection).

III. Antibody Structure

Antibodies comprise a large family of glycoproteins with common structural features. An antibody is comprised of four polypeptides that form a three dimensional structure. Typically, an antibody is comprised of two different polypeptides, the heavy chain and the light chain. An antibody molecule is comprised of one or more of these units, each unit comprising two heavy chains and two light chains. An antibody molecule typically consists of three functional domains: the Fc, Fab, and antigen-binding site.

There are five different types of heavy chain polypeptides designated as α, δ, ε, γ, and μ. There are two different types of light chain polypeptides designated κ and λ. An antibody typically contains only one type of heavy chain and only one type of light chain, although any light chain can associate with any heavy chain.

The carboxyl terminal of each heavy chain polypeptide is known as the constant (Fc) region. The amino terminal of each heavy and light chain polypeptide is known as the variable (V) region. Within the variable regions of the chains are hypervariable regions known as complementarity determining regions (CDRs). The variable regions of one heavy chain and one light chain associate to form an antigen-binding site. Each heavy chain and each light chain includes three CDRs. The six CDRs of an antigen-binding site define the amino acid residues that form the actual binding site for the antigen. CDR variability accounts for the diversity of antigen recognition.

Antibodies against Factor XII may be defined by sequences set forth in Table 1 above.

IV. Antibodies Against fXII

A. Antibody Fragments

Thus, in one embodiment, such molecules will comprise fragments (such as (F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" or bivalent binding molecules. Significantly, such chimeric molecules can contain substituents capable of binding to different epitopes of the same molecule, i.e., fXII, or they can be capable of binding to an distinct molecule, such a another clotting factor or activated protein C epitope.

A single-chain variable fragment (scFv) is another form of antibody fragment. It comprises a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the VH C terminus and an abundance of arginines and prolines at other positions as the only common features of the selected tethers.

The recombinant antibodies against fXII can also involve sequences or moieties that permit dimerization or multimerization of the receptors. Such sequences include those derived from IgA, which permit formation of multimers in conjunction with the J chain. Another multimerization domain is the Gal4 dimerization domain. In other embodiments, the chains can be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, heterobifunctional cross-linkers can be used that eliminate unwanted homopolymer formation. An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker can react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

A cross-linker having reasonable stability in blood can be employed. Numerous types of disulfide-bond containing linkers are known that can be successfully employed to conjugate targeting and therapeutic/preventative agents. Linkers that contain a disulfide bond that is sterically hindered can prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site. The SMPT cross-linking reagent, as with many other known cross-linking reagents, lends the ability to cross-link functional groups such as the SH of cysteine or primary amines (e.g., the epsilon amino group of lysine).

Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxysuccinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987a,b). The use of such cross-linkers is well understood in the art. Another embodiment involves the use of flexible linkers. U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest can be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at 5 least one occurrence of a charged amino acid (e.g., arginine or lysine) followed by a proline, and is characterized by greater stability and reduced aggregation. U.S. Pat. No. 5,880,270 discloses aminooxy-containing linkers useful in a variety of immunodiagnostic and separative techniques.

B. Antibody Conjugates

Further provided are antibody conjugates. For both diagnostic and therapeutic purposes, one can link or covalently bind or complex an agent to an antibody. Such a molecule or moiety can be, but is not limited to, at least one effector or reporter molecule. A reporter molecule is defined as any moiety which can be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and can be termed "immunotoxins."

Antibody conjugates are used as diagnostic agents. Antibody diagnostics generally fall within two classes, those for use in in vitro diagnostics, such as in a variety of immunoassays, and/or those for use in vivo diagnostic protocols, generally known as "antibody-directed imaging."

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being commonly used in certain embodiments, and technicium99m and/or indium$^{111}$ are also often used due to their low energy and suitability for long range detection. Radioactively labeled monoclonal antibodies can be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies can be labeled with technetium$^{99m}$ by ligand exchange process, for example, by reducing pertechnate with stannous solution, chelating the reduced technetium onto a Sephadex column and applying the antibody to this column. Alternatively, direct labeling techniques can be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this can not be advantageous since it results in loss of antigen binding by the antibody conjugate.

Molecules containing azido groups can also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989 and Dholakia et al., 1989) and can be used as antibody binding agents.

Several methods are known in the art for the attachment or conjugation of an antibody to its conjugate moiety. Some attachment methods involve the use of a metal chelate complex employing, for example, an organic chelating agent such as described in U.S. Pat. Nos. 4,472,509 and 4,938,948, each incorporated herein by reference). Monoclonal antibodies can also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succin-imidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature. This approach has been reported to produce diagnostically and therapeutically promising antibodies which are currently in clinical evaluation.

In another embodiment, one may choose to modify the immunoglobulins to improve their stability and half-life in vivo. PEGylation is one such process that involves covalent attachment of polyethylene glycol (PEG) polymer chains to the antibody. PEGylation is routinely achieved by incubation of a reactive derivative of PEG with the target molecule. The covalent attachment of PEG can "mask" the antibody from the host's immune system (reduced immunogenicity and antigenicity), and increase the hydrodynamic size (size in solution) of the agent which prolongs its circulatory time by reducing renal clearance. PEGylation can also provide water solubility. Other polymers used to modify antibodies include polyethyleneimine and polylysine, often linked through succinic acid groups.

C. Immunodetection Methods

In still further embodiments, also provided are immunodetection methods for binding, purifying, removing, quantifying and/or otherwise generally detecting biological components using antibodies that react immunologically with such components. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev (1999) and Gulbis and Galand (1993), each incorporated herein by reference.

In general, the immunobinding methods include obtaining a sample containing a target of interest, and contacting the sample with a first antibody that reacts immunologically with the target under conditions effective to allow the formation of immunocomplexes. The binding of the antibody to the target can then be assessed using a variety of different formats.

In one format, the antibody can be linked to a solid support, such as in the form of a column matrix, and the sample suspected of containing the target will be applied to the immobilized antibody. The unwanted components will be washed from the column, leaving the target immunocomplexed to the immobilized antibody to be eluted.

The immunobinding methods also include methods for detecting and quantifying the amount of an target in a sample and the detection and quantification of any immune complexes formed during the binding process. Here, one would obtain a sample suspected of containing a target, and contact the sample with an antibody against the target, and then detect and quantify the amount of immune complexes formed under the specific conditions.

In terms of antigen detection, the biological sample analyzed can be any sample that is suspected of containing a target, such as, for example, a body fluid like blood, serum, plasma, mucous, urine, saliva, tears or semen. Alternatively, a tissue can be used. Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to targets that react immunologically with antibodies present. After this time, the sample-antibody composition, such as a tissue section, ELISA plate, dot blot or western blot, will generally be washed to remove any non-specifically bound species, allowing only those molecules specifically bound within the primary immune complexes to be detected.

In general, the detection of immunocomplex formation is well known in the art and can be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one can find additional advantages through the use of a secondary binding ligand such as a second antibody and/or a biotin/avidin ligand binding arrangement, as is known in the art.

The antibody employed in the detection can itself be linked to a detectable label, wherein one would then simply detect this label, thereby allowing the amount of the primary immune complexes in the composition to be determined. Alternatively, the first antibody that becomes bound within the primary immune complexes can be detected by means of a second binding ligand that has binding affinity for the antibody. In these cases, the second binding ligand can be linked to a detectable label. The second binding ligand is itself often an antibody, which can thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system can provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

As detailed above, immunoassays, in their most simple and/or direct sense, are binding assays. Certain immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like can also be used. Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a non-specific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions can include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures on the order of 25° C. to 27° C., or can be overnight at about 4° C. or so.

D. Purification

In certain embodiments, the antibodies against fXII can be purified. The term "purified," as used herein, is intended to refer to a composition, isolatable from other components, wherein the protein is purified to any degree relative to its naturally-obtainable state. A purified protein therefore also refers to a protein, free from the environment in which it can naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest can be further purified using chromatographic and electrophoretic techniques to achieve partial or complete purification (or purification to homogeneity).

Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody against fXII, it can be desirable to express the polypeptide in a prokaryotic or eukaryotic expression system and extract the protein using denaturing conditions. The polypeptide can be purified from other cellular components using an affinity column, which binds to a tagged portion of the polypeptide. As is generally known in the art, it is believed that the order of conducting the various purification steps can be changed, or that certain steps can be omitted, and still result in a suitable method for the preparation of a substantially purified protein or peptide.

Commonly, complete antibodies are fractionated utilizing agents (i.e., protein A) that bind the Fc portion of the antibody. Alternatively, antigens can be used to simultaneously purify and select appropriate antibodies. Such methods often utilize the selection agent bound to a support, such as a column, filter or bead. The antibodies is bound to a support, contaminants removed, and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products can vary.

V. Pharmaceutical Compositions and Uses

A. Compositions

Pharmaceutical compositions can comprise an effective amount of one or more antibodies, therapeutic agents or additional agent dissolved or dispersed in a pharmaceutically acceptable carrier. Aqueous compositions comprise an effective amount of the antibody, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologic Standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection or other means via the intravenous, intramuscular, subcutaneous, intranasal, intrapulmonary, intrathecal, or intraperitoneal routes. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability or aerosol delivery exists. It can be incorporated into other drug delivery vehicles designed for extended release, or modified to have an extended biological half life. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The antibodies against fXII can be formulated into a composition in a free base, in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, isotonic agents can be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intranasal, and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, Remington's Pharmaceutical Sciences, 15$^{th}$ Ed. Mack Printing Company, pages 1035-1038 and 1570-1580, 1975). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

The therapeutic agent can comprise different types of carriers depending on whether it is to be administered in solid, liquid or aerosol form, and whether it needs to be sterile for such routes of administration as injection. The antibodies against fXII can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, topically, locally, by inhalation (e.g., aerosol inhalation), by injection, by infusion, by continuous infusion, localized perfusion bathing target cells directly, via a catheter, via a lavage, in cremes, in lipid compositions (e.g., liposomes), or by other methods or any combination of the foregoing as would be known to one of ordinary skill in the art (see, for example, Remington's Pharmaceutical Sciences, 18th Ed. Mack Printing Company, 1990, incorporated herein by reference).

The actual dosage amount of a composition administered to an animal patient can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

In certain embodiments, pharmaceutical compositions can comprise, for example, at least about 0.1% of an active compound. In other embodiments, an active compound can comprise between about 2% to about 75% of the weight of the unit, or between about 25% to about 60%, for example, and any range derivable therein.

In any case, the composition can comprise various antioxidants to retard oxidation of one or more component. In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, isotonic agents can be included, such as, for example, sugars, sodium chloride or combinations thereof.

In other embodiments, one can use eye drops, nasal solutions or sprays, aerosols or inhalants. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in some embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, can be included in the formulation. For example, various commercial nasal preparations are known and include drugs such as antibiotics or antihistamines.

In certain embodiments the antibodies are prepared for administration by such routes as oral ingestion. In these embodiments, the solid composition can comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions can be incorporated directly with the food of the diet. Carriers for oral administration comprise inert diluents, assimilable edible carriers or combinations thereof. In other embodiments, the oral composition can be prepared as a syrup or elixir. A syrup or elixir, can comprise, for example, at least one active agent, a sweetening agent, a preservative, a flavoring agent, a dye, a preservative, or combinations thereof.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

B. Pharmaceutical Uses

The antibodies of the present application, which prevent fXII activation, are inherently safe given that fXII deficiency is asymptomatic in humans and mice. This is a major advance relative to using other anticoagulant antibodies because antibodies other than those discussed here (i.e., other than those inhibiting contact activation of fXI) are expected to cause bleeding disorders regardless of their route of administration or dosage. Antibodies like those disclosed here will not have such adverse affects on hemostasis given that fXII does not participate in vital hemostasis. Indeed, the danger from overdose is theoretically zero because it has no additional effect beyond saturation of its target. Thus, the antibodies of the present application are safe anti-thrombotics (anticoagulant, blood-thinner).

The pharmaceutical compositions can be, in generaly, parenterally administered to subjects suffering from diseases in which fXII activation is problematic. The compositions can be administered to patients in need as a bolus or by continuous infusion. For example, a bolus administration of an inventive antibody present as a Fab fragment can be in an amount of from 0.0025 to 100 mg/kg body weight, 0.025 to 0.25 mg/kg, 0.010 to 0.10 mg/kg or 0.10-0.50 mg/kg. For continuous infusion, an inventive antibody present as an Fab fragment can be administered at 0.001 to 100 mg/kg body weight/minute, 0.0125 to 1.25 mg/kg/min., 0.010 to 0.75 mg/kg/min., 0.010 to 1.0 mg/kg/min. or 0.10-0.50 mg/kg/min. for a period of 1-24 hours, 1-12 hours, 2-12 hours, 6-12 hours, 2-8 hours, or 1-2 hours. For administration of an inventive antibody present as a full-length antibody (with full constant regions), dosage amounts can be about 0.1-20 mg/kg body weight, 1-10 mg/kg, or 2-5 mg/kg. Such full-length antibodies would typically be administered by bolus injections, repeated hourly, daily, weekly, or monthly as a function of dose. The frequency and duration of the administration would depend upon the severity of the condition and the need for continued therapeutic activity, without limitation. Frequency could also range from three times per week to once every two weeks to six months.

Additionally, the compositions can be administered to patients via subcutaneous, intravenous, or intramuscular injection. For example, a dose of 10 to 100 mg anti-fXII antibody can be administered to patients via subcutaneous injection daily, weekly, biweekly or monthly.

As used herein, "therapeutically effective amount" means an amount of an anti-fXII monoclonal antibody or of a combination of such antibody with another anticoagulant or antithrombotic agent that is needed to effectively inhibit thrombosis in vivo or otherwise cause a measurable benefit in vivo to a patient in need. The precise amount will depend upon numerous factors, including, but not limited to the components and physical characteristics of the therapeutic composition, intended patient population, individual patient considerations, and the like, and can readily be determined by one skilled in the art.

1. Thrombosis and Thromboembolism

Thrombosis is the formation of a blood clot inside a blood vessel, obstructing the flow of blood through the circulatory system. When a blood vessel is injured, the body uses platelets (thrombocytes) and fibrin to form a blood clot to prevent blood loss. Even when a blood vessel is not injured, blood clots may form in the body under certain conditions. A clot that breaks free and begins to travel around the body is known as an embolus. When a thrombus occupies more than 75% of cross-sectional area of the lumen of an artery, blood flow to the tissue supplied is reduced enough to cause symptoms because of decreased oxygen (hypoxia) and accumulation of metabolic products like lactic acid. More than 90% obstruction can result in anoxia, the complete deprivation of oxygen, and infarction, a mode of cell death. Thromboembolism is the combination of thrombosis and its main complication, embolism.

There are two distinct forms of thrombosis, venous thrombosis and arterial thrombosis, each of which can be presented by several subtypes. Venous thrombosis is the formation of a thrombus (blood clot) within a vein. There are several diseases which can be classified under this category.

Deep vein thrombosis (DVT) is the formation of a blood clot within a deep vein. It most commonly affects leg veins, such as the femoral vein. Three factors are important in the formation of a blood clot within a deep vein—these are the rate of blood flow, the thickness of the blood and qualities of the vessel wall. Classical signs of DVT include swelling, pain and redness of the affected area.

Portal vein thrombosis is a form of venous thrombosis affecting the hepatic portal vein, which can lead to portal hypertension and reduction of the blood supply to the liver. It usually has a pathological cause such as pancreatitis, cirrhosis, diverticulitis or cholangiocarcinoma.

Renal vein thrombosis is the obstruction of the renal vein by a thrombus. This tends to lead to reduced drainage from the kidney. Anticoagulation therapy is the treatment of choice.

Jugular vein thrombosis is a condition that may occur due to infection, intravenous drug use or malignancy. Jugular vein thrombosis can have a varying list of complications, including: systemic sepsis, pulmonary embolism, and papilledema. Though characterized by a sharp pain at the site of the vein, it can prove difficult to diagnose, because it can occur at random.

Budd-Chiari syndrome is the blockage of the hepatic vein or the inferior vena cava. This form of thrombosis presents with abdominal pain, ascites and hepatomegaly. Treatment varies between therapy and surgical intervention by the use of shunts.

Paget-Schroetter disease is the obstruction of an upper extremity vein (such as the axillary vein or subclavian vein) by a thrombus. The condition usually comes to light after vigorous exercise and usually presents in younger, otherwise healthy people. Men are affected more than women.

Cerebral venous sinus thrombosis (CVST) is a rare form of stroke which results from the blockage of the dural venous sinuses by a thrombus. Symptoms may include headache, abnormal vision, any of the symptoms of stroke such as weakness of the face and limbs on one side of the body and seizures. The diagnosis is usually made with a CT or MRI scan. The majority of persons affected make a full recovery. The mortality rate is 4.3%.

Arterial thrombosis is the formation of a thrombus within an artery. In most cases, arterial thrombosis follows rupture of atheroma, and is therefore referred to as atherothrombosis. Another common cause of arterial thrombosis is atrial fibrillation, which causes disturbed blood flow. In addition, it is well known that the direct current cardioversion of atrial fibrillation carries a great risk of thromboembolism, especially if persisting more than 48 hours. Thromboembolism strikes approximately 5% of cases not receiving anticoagulant therapy. The mechanism and pathogenesis of thromboembolism after cardioversion is not completely understood. Arterial thrombosis can embolize and is a major cause of arterial embolism, potentially causing infarction of almost any organ in the body.

Hepatic artery thrombosis usually occurs as a devastating complication after liver transplantation. An arterial embolus can also form in the limbs.

Thus, actual bleeding in patients with thrombosis, e.g., those that are bleeding due to another drug, or any other cause, inherited or acquired, can be safely treated. Also, foreign body-associated thrombosis, e.g., that associated with extracorporeal devices, oxygenators, dialysis membranes, catheters, intravascular objects (e.g., stents, grafts) may be safely treated, particularly when other drugs are contraindicated.

2. Dissementated Intravascular Coagulation or Consumptive Coagulopathy

Consumptive coagulopathy (CC), also known as disseminated intravascular coagulation (DIC) or disseminated intravascular coagulopathy, is a pathological activation of coagulation (blood clotting) mechanisms that happens in response to a variety of diseases. DIC leads to the formation of small blood clots inside the blood vessels throughout the body. As the small clots consume coagulation proteins and platelets, normal coagulation is disrupted and abnormal bleeding occurs from the skin (e.g., from sites where blood samples were taken), the gastrointestinal tract, the respiratory tract and surgical wounds. The small clots also disrupt normal blood flow to organs (such as the kidneys), which may malfunction as a result.

DIC can occur acutely but also on a slower, chronic basis, depending on the underlying problem. It is common in the critically ill, and may participate in the development of multiple organ failure, which may lead to death.

Under homeostatic conditions, the body is maintained in a finely tuned balance of coagulation and fibrinolysis. The activation of the coagulation cascade yields thrombin that converts fibrinogen to fibrin; the stable fibrin clot being the final product of hemostasis. The fibrinolytic system then functions to break down fibrinogen and fibrin. Activation of the fibrinolytic system generates plasmin (in the presence of thrombin), which is responsible for the lysis of fibrin clots. The breakdown of fibrinogen and fibrin results in polypeptides called fibrin degradation products (FDPs) or fibrin split products (FSPs). In a state of homeostasis, the presence of plasmin is critical, as it is the central proteolytic enzyme of coagulation and is also necessary for the breakdown of clots, or fibrinolysis.

In DIC, the processes of coagulation and fibrinolysis are dysregulated, and the result is widespread clotting with resultant bleeding. Regardless of the triggering event of DIC, once initiated, the pathophysiology of DIC is similar in all conditions. One critical mediator of DIC is the release of a transmembrane glycoprotein called tissue factor (TF). TF is present on the surface of many cell types (including endothelial cells, macrophages, and monocytes) and is not normally in contact with the general circulation, but is exposed to the circulation after vascular damage. For example, TF is released in response to exposure to cytokines (particularly interleukin 1), tumor necrosis factor, and endotoxin. This plays a major role in the development of DIC in septic conditions. TF is also abundant in tissues of the lungs, brain, and placenta. This helps to explain why DIC readily develops in patients with extensive trauma. Upon activation, TF binds with coagulation factors which then triggers the extrinsic pathway (via fVII) which subsequently triggers the intrinsic pathway (XII to XI to IX) of coagulation.

The release of endotoxin is the mechanism by which Gram-negative sepsis provokes DIC. In acute promyelocytic leukemia, treatment causes the destruction of leukemic granulocyte precursors, resulting in the release of large amounts of proteolytic enzymes from their storage granules, causing microvascular damage. Other malignancies may enhance the expression of various oncogenes that result in the release of TF and plasminogen activator inhibitor-1 (PAI-1), which prevents fibrinolysis.

Excess thrombin in the circulation results from the excess activation of the coagulation cascade. The excess thrombin cleaves fibrinogen, which ultimately leaves behind multiple fibrin clots in the circulation. These excess clots trap platelets to become larger clots, which leads to microvascular and macrovascular thrombosis. This lodging of clots in the microcirculation, in the large vessels, and in the organs is what leads to the ischemia, impaired organ perfusion, and end-organ damage that occurs with DIC.

Coagulation inhibitors are also consumed in this process. Decreased inhibitor levels will permit more clotting so that a feedback system develops in which increased clotting leads to more clotting. At the same time, thrombocytopenia occurs and this has been attributed to the entrapment and consumption of platelets. Clotting factors are consumed in the development of multiple clots, which contributes to the bleeding seen with DIC.

Simultaneously, excess circulating thrombin assists in the conversion of plasminogen to plasmin, resulting in fibrinolysis. The breakdown of clots results in excess amounts of FDPs, which have powerful anticoagulant properties, contributing to hemorrhage. The excess plasmin also activates the complement and kinin systems. Activation of these systems leads to many of the clinical symptoms that patients experiencing DIC exhibit, such as shock, hypotension, and increased vascular permeability. The acute form of DIC is considered an extreme expression of the intravascular coagulation process with a complete breakdown of the normal homeostatic boundaries. DIC is associated with a poor prognosis and a high mortality rate.

There has been a recent challenge however to the basic assumptions and interpretations of the pathophysiology of DIC. A study of sepsis and DIC in animal models has shown that a highly-expressed receptor on the surface of hepatocytes, termed the Ashwell-Morell receptor, is responsible for thrombocytopenia in bacteremia and sepsis due to streptococcal pneumoniae (SPN) and possibly other pathogens. The thrombocytopenia observed in SPN sepsis was not due to increased consumption of coagulation factors such as platelets, but instead was the result of this receptor's activity enabling hepatocytes to ingest and rapidly clear platelets from circulation. By removing pro-thrombotic components before they participate in the coagulopathy of DIC, the Ashwell-Morell receptor lessens the severity of DIC, reducing thrombosis and tissue necrosis, and promoting survival. The hemorrhage observed in DIC and among some tissues lacking this receptor may thereby be secondary to increased thrombosis with loss of the mechanical vascular barrier. This discovery has possible significant clinical implications in devising new approaches to reducing the pathophysiology of DIC.

The only effective treatment is the reversal of the underlying cause. Anticoagulants are given exceedingly rarely when thrombus formation is likely to lead to imminent death (such as in coronary artery thrombosis or cerebrovascular thrombosis). Platelets may be transfused if counts are less than 5,000-10,000/mm$^3$ and massive hemorrhage is occurring, and fresh frozen plasma may be administered in an attempt to replenish coagulation factors and anti-thrombotic factors, although these are only temporizing measures and may result in the increased development of thrombosis.

DIC results in lower fibrinogen levels (as it has all been converted to fibrin), and this can be tested for in the hospital lab. A more specific test is for "fibrin split products" (FSPs) or "fibrin degradation products" (FDPs) which are produced when fibrin undergoes degradation when blood clots are dissolved by fibrinolysis. In some situations, infusion with antithrombin may be necessary.

3. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present invention provides for the safe treatment of bleeding in trauma patients, including both pre-treatment (in the case of a medical procedure) and treatment after trauma injury as occurred.

Surgery.

Surgery uses operative manual and instrumental techniques on a patient to investigate and/or treat a pathological condition such as disease or injury, to help improve bodily function or appearance, or sometimes for some other reason. The present invention can safely address trauma resulting from surgeries, including peri-surgical and peri-interventional thromboprophylaxis, especially when the risk of bleeding is high. Two particular areas of concern are surgeries relating to the nervous system and the eye.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called non-invasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

Traumatic Hemorrhage.

Traumatic hemorrhage accounts for much of the wide ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provide. Finally, the critical care phase provides for post-operative support and tissue perfusion.

4. Device Implantation

An implant is a medical device manufactured to replace a missing biological structure, support a damaged biological structure, or enhance an existing biological structure. Medical implants are man-made devices, in contrast to a transplant, which is a transplanted biomedical tissue. The surface of implants that contact the body might be made of a biomedical material such as titanium, silicone or apatite depending on what is the most functional. In some cases implants contain electronics, e.g., artificial pacemaker and cochlear implants. Some implants are bioactive, such as subcutaneous drug delivery devices in the form of implantable pills or drug-eluting stents.

Among the most common types of medical implants are the pins, rods, screws and plates used to anchor fractured bones while they heal. More complex implants include artificial joints, such has knee and hip joints, breast implants, artificial heart valves, stents and catheters.

5. Transplant

Organ transplantation an organ from one body to another or from a donor site on the patient's own body, for the purpose of replacing the recipient's damaged or absent organ. The emerging field of regenerative medicine is allowing scientists and engineers to create organs to be re-grown from the patient's own cells (stem cells, or cells extracted from the failing organs). Organs and/or tissues that are transplanted within the same person's body are called autografts. Transplants that are recently performed between two subjects of the same species are called allografts. Allografts can either be from a living or cadaveric source.

Organs that typically can be transplanted are the heart, kidneys, liver, lungs, pancreas, intestine, and thymus. Tissues include bones, tendons (both referred to as musculoskeletal grafts), cornea, skin, heart valves, and veins. Worldwide, the kidneys are the most commonly transplanted organs, followed closely by the liver and then the heart. The cornea and musculoskeletal grafts are the most commonly transplanted tissues; these outnumber organ transplants by more than ten-fold.

Organ donors may be living, or brain dead. Tissue may be recovered from donors who are cardiac dead—up to 24 hours past the cessation of heartbeat. Unlike organs, most tissues (with the exception of corneas) can be preserved and stored for up to five years, meaning they can be "banked." In the United States of America, tissue transplants are regulated by the U.S. Food and Drug Administration (FDA) which sets strict regulations on the safety of the transplants, primarily aimed at the prevention of the spread of communicable disease. Regulations include criteria for donor screening and testing as well as strict regulations on the processing and distribution of tissue grafts. Organ transplants are not regulated by the FDA.

Transplantation medicine is one of the most challenging and complex areas of modern medicine. In addition to the key problem of transplant rejection, thrombosis resulting from clotting at the site of surgery followed by transport of the clot into the vasculature is a major concern.

6. Cancer

A diversity of coagulation disorders in cancer patients arise from tumor-specific growth characteristics, neoangiogenesis with impaired endothelial lining, defective myelopoiesis, hypoproteinemia or metastatic lesions growth with organ dysfunction. Recent investigations have found a clinically relevant correlation of coagulation disorders and tumor growth. These prompted new therapeutic strategies focused on growth factors with the aim to control tumor metastasis, particularly if used for the treatment of micro-metastatic disease. However, such treatment may lead to the life threatening coagulation imbalance.

Indeed, some cancers express more thrombogenic proteins than normal cells. These proteins include tissue factor, collagen, laminin, factors VII, XI, and XII, plasminogen activator inhibitor, antithrombin, vitronectin, fibronectin, and fibrinogen. These proteins may appear on the cancer cell surface or may be secreted, and can trigger cancer-associated thrombosis, which is quite frequent among cancer patients. Safe anticoagulation with antibodies of the present disclosure may assist some cancer patients with compromised hemostasis.

A coagulation homeostasis may become further impaired after nonsurgical cancer therapy, especially after preoperative irradiation, which produces lesions precipitating both bleeding and thrombosis. Anticancer chemotherapy may affect liver function and decrease the synthesis of both procoagulation and anticoagulation factors. Most chemotherapeutic protocols affect platelet synthesis, which arises as a principal dose-limiting side effect. This was observed both during combined systemic chemotherapy and local antitumor therapy. Although the side effects produced by chemotherapy are reversible, endothelial lesions may persist for many years after the anticancer treatment. Furthermore, some patients have low platelet count during chemotherapy, and these patients are at risk of bleeding, but still may need to be treated for thrombosis.

7. Stroke and Myocardial Infarction

A stroke is the rapid decline of brain function due to a disturbance in the supply of blood to the brain. This can be due to ischemia, thrombus, embolus (a lodged particle) or hemorrhage (a bleed). In thrombotic stroke, a thrombus (blood clot) usually forms around atherosclerotic plaques. Since blockage of the artery is gradual, onset of symptomatic thrombotic strokes is slower. Thrombotic stroke can be divided into two categories—large vessel disease and small vessel disease. The former affects vessels such as the internal carotids, vertebral and the circle of Willis. The latter can affect smaller vessels such as the branches of the circle of Willis.

Myocardial infarction (MI) is caused by an infarct (death of tissue due to ischemia), often due to the obstruction of a coronary artery by a thrombus. MI can quickly become fatal if emergency medical treatment is not received promptly. If diagnosed within 12 hours of the initial episode (attack) then thrombolytic therapy is initiated.

8. Infection

If an infection is present at the site of thrombosis, the thrombus may break down, spreading particles of infected material throughout the circulatory system (pyemia, septic embolus) and setting up metastatic abscesses wherever they come to rest. Without an infection, the thrombus may become detached and enter circulation as an embolus, finally lodging in and completely obstructing a blood vessel, which unless treated very quickly will lead to tissue necrosis (an infarction) in the area past the occlusion. If the occlusion is in the coronary artery, myocardial ischaemia is likely to occur, whereby cardiac myocytes cannot function properly due to lack of oxygen. This lack of oxygen is then likely to result in a myocardial infarction.

9. Combination Therapy

The antibodies of the present invention can be used as monotherapy, but may be combined with other therapies. For example, co-administration of one or more additional antithrombotic agents, such as platelet inhibitors, anticoagulants, or thrombolytic agents is believed useful for treating certain coagulopathies. These combination therapies are likely to reduce the necessary infusion frequency of the anti-clotting drugs. By co-administration or combination therapy is meant administration of the two therapeutic drugs each formulated separately or formulated together in one composition, and, when formulated separately, administered either at approximately the same time or at different times, but over the same therapeutic period.

VI. Kits

Any of the compositions described herein can be comprised in a kit. The kits will thus comprise, in suitable container, an antibody and/or an additional agent. Other components can be included in a kit. Diagnostic and therapeutic kits comprise in suitable container, a pharmaceutically acceptable formulation of an antibody in a pharmaceutically acceptable formulation. The kit can have a single container, and/or it can have distinct container for each compound.

When the components of the kit are provided in one and/or more liquid solutions, the liquid solution is an aqueous solution, with a sterile aqueous solution being one example of a particular embodiment. The antibody can also be formulated into a syringeable composition, in which case, the container can itself be a syringe, pipette, and/or other such like apparatus, from which the formulation can be applied to an infected area of the body, injected into an animal, and/or even applied to and/or mixed with the other components of the kit.

However, the components of the kit can be provided as dried powder(s). When reagents and/or components are provided as a dry powder, the powder can be reconstituted by the addition of a suitable solvent. It is envisioned that the solvent can also be provided in another container.

The container will generally include at least one vial, test tube, flask, bottle, syringe and/or other container, into which the antibody/antibody formulation is placed, suitably allocated. The kits can also comprise a second container for containing a sterile, pharmaceutically acceptable buffer and/or other diluent.

The kits can also include a means for containing the vials in close confinement for commercial sale, such as, e.g., injection and/or blow-molded plastic containers into which the desired vials are retained.

Irrespective of the number and/or type of containers, the kits can also comprise, and/or be packaged with, an instrument for assisting with the injection/administration and/or placement of the ultimate antibody within the body of an animal. Such an instrument can be a syringe, pipette, forceps, and/or any such medically approved delivery vehicle.

VII. Examples

The following examples are included to demonstrate embodiments. It should be appreciated by those of skill in the art that the techniques disclosed in the examples which follow represent techniques discovered by the inventor to function well in the practice, and thus can be considered to constitute modes for its practice. However, those of skill in the art should, in light of the present disclosure, appreciate that many changes can be made in the specific embodiments which are disclosed and still obtain a like or similar result without departing from the spirit and scope.

Example 1

Materials and Methods

Antibody Production and Testing.

AB042 and AB043 were generated in fXII knockout mice by immunizing with human fXII, and clones were isolated clones using standard methods. Strong binders (48 clones) were selected for in vitro testing of neutralizing capacity. Of these, two clones were found to have the desirable properties: inhibition of human plasma coagulation and cross-reactivity with baboon plasma. No cross-reactivity with several other mammalian species (potential test species) was found. The positives were hybridized, and then produced in larger quantities (>300 mg) in disposable bioreactors, then purified for animal testing and in vitro characterization. AB042 was tested in baboons, and both AB042 and AB043 were tested in fXII deficient mice that were reconstituted with human fXII.

Materials.

TRIzol® Plus RNA Purification System (Invitrogen, Cat. No.: 15596-026);
SuperScript™ III First-Strand Synthesis System (Invitrogen, Cat. No.: 18080-051).

Total RNA Extraction.

Total RNA was isolated from hybridoma cells following the technical manual of TRIzol® Plus RNA Purification System. The total RNA was analyzed by agarose gel electrophoresis.

RT-PCR.

Total RNA was reverse transcribed into cDNA using isotype-specific anti-sense primers or universal primers following the technical manual of SuperScript™ III First-Strand Synthesis System. The antibody fragment was amplified according to the standard operating procedure of RACE of GenScript.

Cloning of Antibody Genes.

Amplified antibody (VH, VL, CH and CL) genes were separately cloned into a standard cloning vector owned by GenScript using standard molecular cloning procedures.

Screening and Sequencing.

Colony PCR screening was performed to identify clones with inserts of correct sizes. No less than ten independent positive colonies were sequenced for each antibody fragment.

Example 2

Results

FIG. 1A shows Western blots of human (H) and baboon (B) plasma size fractionated by SDS-PAGE using a polyclonal anti-fXII antibody, AB042 or AB043 as the detection antibody. AB043 and AB042 both recognize baboon and human fXII, indicating they can be used for studies in baboon thrombosis models. FIG. 1B shows schematic diagrams of human FXII and hepatoctye growth factor activator (HGFA). Chimeras in which individual fXII domains were replaced with those of HGFA were expressed in human fibroblasts. FIG. 1C shows western blots of fXII and FXII/HGFA chimeras size fractionated by SDS-PAGE using a polyclonal anti-fXII antibody, AB042 or AB043 as the detection antibody. AB043 does not recognize the chimeras for the fibronectin type I domain or the EGF2 domain, while the AB042 does not recognize the EGF2 or kringle domain chimeras. This indicates that the two antibodies likely have different binding epitopes.

FIGS. 2A-C demonstrate that AB043 and AB042 interfere with fXII activation. In a standard aPTT assay (FIG. 2A), both antibodies prolonged time to clot formation, while the combination of both antibodies had a greater effect than either antibody alone. However, when fXIIa was incubated with antibody for 15 minutes prior to adding it to plasma (FIG. 2B), the antibodies had minimal effect, indicating that once fXIIa is generated, they do not affect its ability to activate fXI. fXII activation to fXIIa in the presence of the aPTT reagent was followed using a chromogenic substrate cleavage assay (FIG. 2C). It was found that the antibodies interfere with surface dependent fXII "autoactivation".

FIGS. 3A-C show the effects of AB043 and AB042 on prekallikrein (PK) and fXI activation by fXIIa. FXIIa was inhibited after incubation with these proteins by addition of corn trypsin inhibitor. The formation of kallikrein (the active form of PK), and fXIa (the active form of fXI) were identified by chromogenic substrate assay. Neither AB043 nor AB042 had a discernible effect on PK activation by fXIIa (FIG. 3A), while fXI activation was modestly inhibited by AB042 (~50% reduction—FIG. 3B). In FIG. 3C, the effect of the antibodies on reciprocal activation of fXII and PK is shown. Here trace amounts of fXIIa and kallikrein in the FXII and PK preparations sets off a cycle of reciprocal activation in the absence of a surface that is followed with a chromogenic substrate assay. Here AB043 and AB042 appear to slow the reciprocal activation by ~50%. This is further evidence that these antibodies impact fXII primarily by limiting its activation.

FIGS. 4A-B show that AB043 and AB042 enhance fXII activation by fXIa (FIG. 4A) and kallikrein (FIG. 4B). kallikrein is a potent activator of fXII, while fXIa has some activity in this regard. Binding of the antibodies to fXII apparently changes its conformation, making the protein a more suitable substrate for these proteases. However, this effect appears to be minimal in plasma, as the main effect of the antibodies in clotting assays is to blunt coagulation by preventing fXII from becoming activated, which subsequently limits the amount of kallikrein and fXIa available in the system.

FIG. 5 shows the effects of AB043 and AB042 on polyphosphate-induced fXII activation. Polyphosphate (poly-P) was recently recognized as a likely physiologically relevant modifier of blood coagulation. It is capable of inducing activation of both fXII and fXI. Both antibodies inhibit fXII activation in the presence of poly-P, but in contrast to reactions in the presence of silica (FIG. 2C), AB043 may have a somewhat greater effect than AB042.

FIG. 6 shows the effect of AB043 and AB042 on arterial thrombosis in mice. Factor XII-deficient mice that received infusions of human fXII all developed arterial occlusion in the FeCl3-injury model, similar to wild-type mice. If the mice receiving human fXII were treated with AB042, vessel occlusion did not occur in response to FeCl3. With AB043, only half of the animals developed occlusion.

Figure 7:
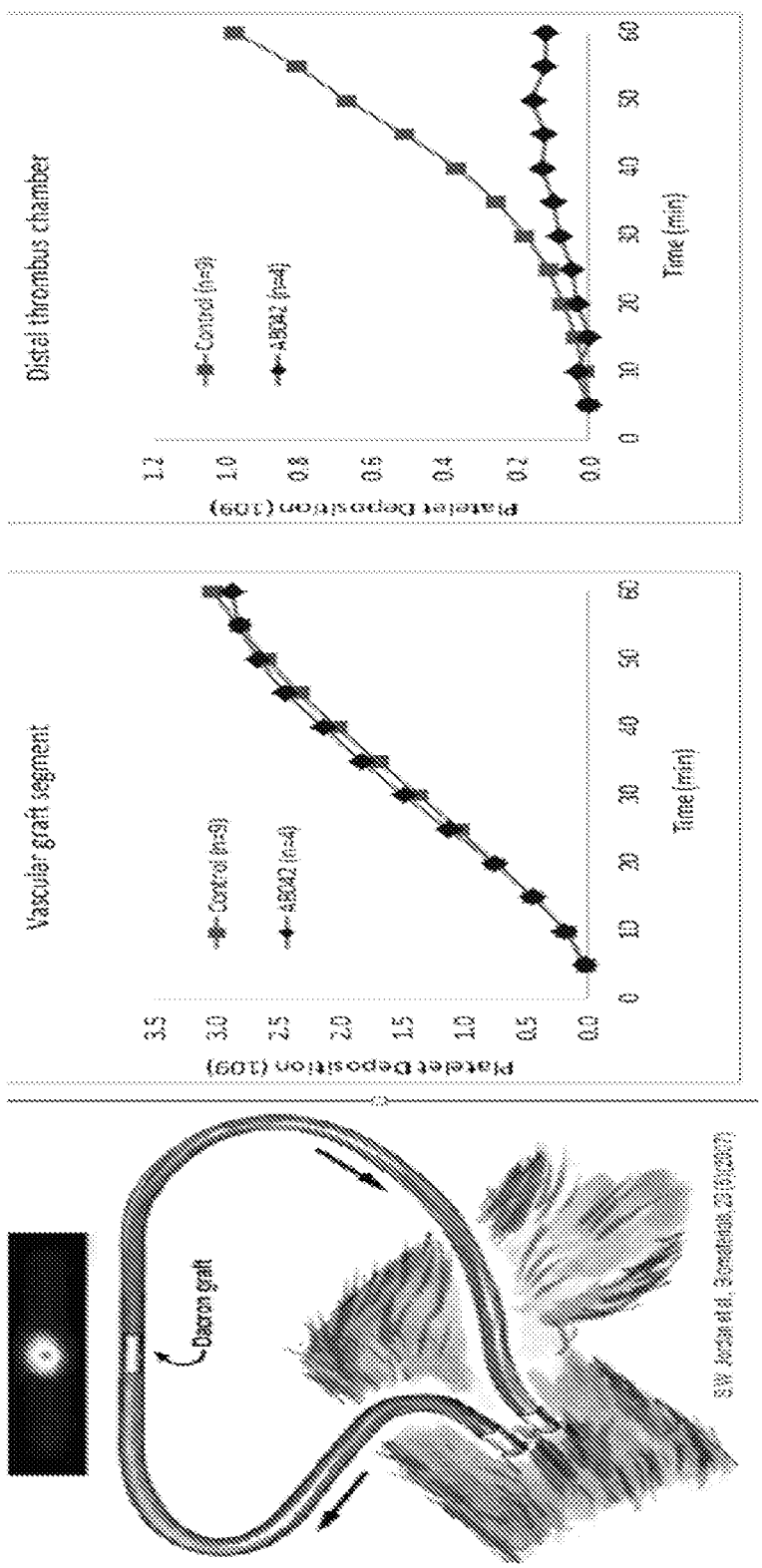
FIG. 7. Baboon arterio-venous shunt thrombosis model. A collagen-coated ePTFE graft (4 mm internal diameter, 20 mm long) inserted into a silicone sleve (9 mm internal diameter) was deployed into a chronic AV shunt in male baboons (*Papio anubis*) before (Control) or after administration of AB042. AB042 (5-6 mg/kg i.v. bolus) was administered one hour before insertion of the thrombogenic graft to allow time for distribution and equilibrium. The initial average wall shear rates in the graft and the downstream thrombus chamber chamber (within the silicon sleeve) were ~265/sec and 30/sec respectively. These shear rates are within the range of measured average shear rates in the human brachial artery and femoral vein, respectively.
Figure 9:
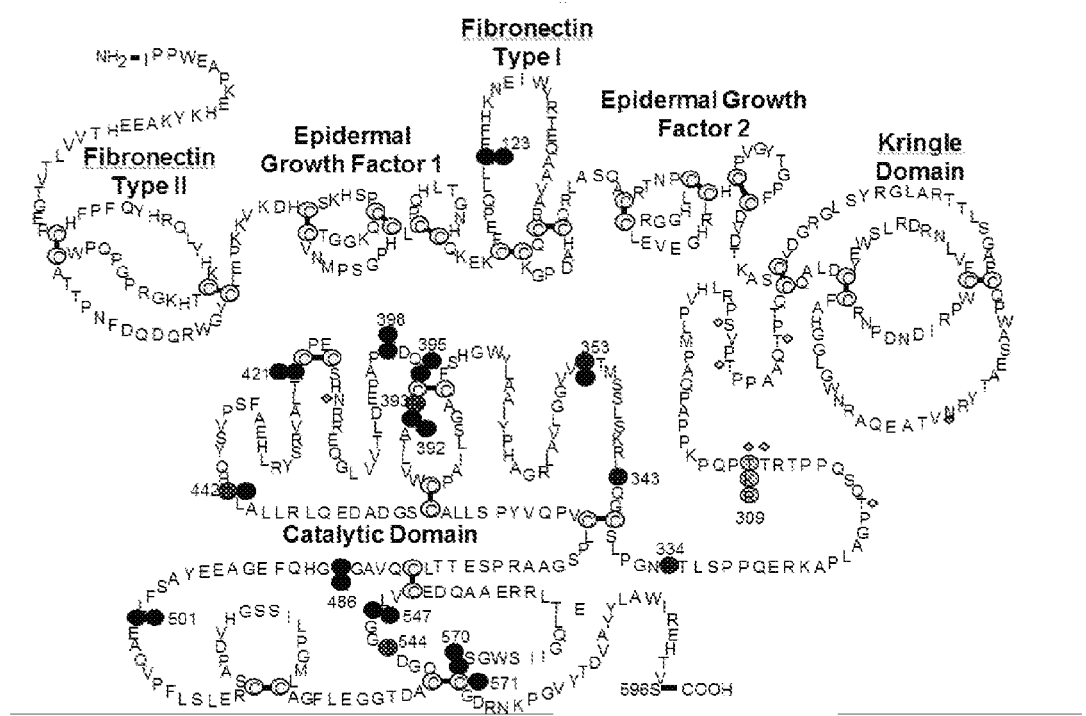
FIG. 9. Domain structure of human fXII. Shown are the fibronectin type II domain, epidermal growth factor domain 1, fibronectin type I domain, epidermal growth factor domain 2, kringle domain, proline rich region, and trypsin-like protease domain. Conversion of fXII to fXIIa requires cleavage after Arg353. FXII is a homolog of a more ancient molecule—hepatocyte growth factor activator (HGFA). The domain structure of HGFA is identical to fXII except that in place of the proline rich region of fXII there is a shorter sequence without an abundance of proline.

FIG. 7. shows a baboon arterio-venous shunt thrombosis model. Collagen coated vascular grafts were inserted into temporary arterio-venous shunts in baboons (left panel). The grafts are very thrombogenic, and their insertion results in platelet and fibrin accumulation within the graft (middle panel) and in a chamber downstream of the graft (right panel). Administering AB042 prior to insertion of the graft markedly reduces thrombus formation down stream of the graft, indicating a potent antithrombotic effect. It is not surprising that there was no effect on thrombus accumulation within the graft, as the level of anticoagulation typically required to prevent thrombus formation in this location results in significant bleeding.

FIG. 8 shows a human ex vivo blood flow model using recalcified human whole blood perfused through collagen-coated capillary tubes. In the absence of an anti-fXII antibody, there is significant accumulation of fibrin and platelets within the tube, eventually leading to occlusion of the tube. This process is significantly inhibited by AB043 and AB042, maintaining tube patency. AB042 may be slightly more effective than AB043 at limiting fibrin formation (orange signal).

Taken as a whole, these data demonstrate that monoclonal antibodies AB043 and AB042 bind to the fXII/XIIa non-catalytic heavy chain at different sites, and inhibit activation of fXII on polyanionic surfaces. Combining the antibodies produced an additive effect on inhibition of fXII activation, consistent with the antibodies having different binding sites on fXII. AB043 is more effective than AB042 at inhibiting fXII activation when polyphosphate is the anionic surface, while AB042 is more effective with a silica based aPTT reagent. The antibodies had, at most, modest effect on fXIIa activation of fXI, and no effect on activation of prekallikrein. AB042 prevented ferric chloride-induced thrombus formation in mice reconstituted with human fXII, while AB043 reduced the rate of thrombotic occlusion by 50%. AB042 also reduced platelet-rich thrombus accumulation in a baboon thrombosis model. In a flow model using human blood, both AB043 and AB042 significantly inhibited fibrin formation and subsequent platelet accumulation, maintaining patency of the capillary tube.

Sequencing.

The isolated total RNA of the sample was run alongside a DNA Marker III (TIANGEN Cat. No. MD103) on a 1.5% agarose/GelRed™ gel. Following PCR, four microliters of PCR products were run alongside the DNA Marker III on a 1.5% agarose/GelRed™ gel. The PCR products were purified and stored at −20° C. Ten clones with insertions of $V_H$, $V_L$, $C_H$ and $C_L$ genes were sent for sequencing of the antibody fragments. The $V_H$, $V_L$, $C_H$ and $C_L$ genes were found nearly identical. Their consensus sequence is believed to be the sequence of the antibody produced by the hybridoma AB042.

Example 3

Discussion

The plasma protease fXIIa contributes to vascular occlusion in murine thrombosis models. FXII, the precursor of fXIIa, is traditionally considered a part of the blood coagulation mechanism, although total deficiency of fXII is not associated with a bleeding disorder. The observation that fXII deficient mice do not bleed abnormally after trauma, but are protected from thrombosis, has generated considerable interest in developing drugs that target fXII or fXIIa to treat or prevent thrombotic disorders. FXIIa appears to contribute to thrombosis by activating the protein fXI to form the protease fXIa. FXI deficient mice, like fXII deficient mice, are also resistant to thrombosis. While there is good correlation between plasma fXI levels and risk of thrombotic events in humans, the situation is not as clear for fXII. This raises the possibility that there are fundamental differences in thrombus formation in mice and humans.

To facilitate studies on the effects of fXII and fXIIa on thrombus formation in primates and in human blood, the inventors developed novel inhibitory antibodies to human fXII, designated AB043 and AB042, by immunizing fXII-deficient mice with human fXII. The binding sites for these antibodies were studied using recombinant human fXII molecules that lack various domains, and chimeras in which specific fXII domains are replaced with those from the related protein hepatocyte growth factor activator. AB043 and AB042 both bind to the fXII/fXIIa non-catalytic heavy chain, but at different sites on the heavy chain. AB043 binds on or near the EGF2 domain, while AB042 binds to the fibronectin type I and/or kringle domain. These areas have been implicated in fXII binding to polyanionic surfaces, an interaction that is critical for fXII conversion to fXIIa. Saturating concentrations of AB043 or AB042 reduced fXII activity by ~50% and ~90%, respectively, in an aPTT assay using normal human plasma, while combining the antibodies resulted in >95% inhibition. However, in assays in which clot formation was triggered by adding fXIIa directly to plasma, preincubation of fXIIa with either antibody did not prolong the clotting time. Furthermore, neither antibody had a strong effect in a chromogenic assay of fXI activation by fXIIa, indicating the antibodies interfere with the aPTT assay primarily by inhibiting fXII activation.

FXII activation in the aPTT assay is typically initiated by addition of a polyanion such as silica to the plasma to induce contact activation. In vivo, polymers of inorganic phosphate (polyP) may serve a similar function. Contact activation is triggered in plasma when fXII bound to the polyanion is activated, probably by trace amounts of fXIIa or another protease present in the plasma. Once formed, fXIIa converts the zymogens prekallikrein and fXI to the proteases kallikrein and fXIa, both of which can activate additional fXIIa to amplify the process. In the presence of AB043 or AB042, activation of fXII in the presence of either silica or the more physiologically relevant polyP was significantly reduced. Interestingly, the antibodies actually potentiated fXII activation by kallikrein or fXIa in the absence of a polyanion. Taken as a whole, these results suggest that binding of AB043 or AB042 to fXII results in conformational changes that make fXII a better substrate for kallikrein and fXIa, possibly by mimicking the effect of FXII binding to a polyanion, but that prevent activation of fXII by fXIIa (autoactivation), blunting the overall rate of activation.

The effects of AB043 and AB042 were tested in a mouse model in which thrombotic occlusion of the carotid artery is induced by exposing the vessel to a 3.5% solution of ferric chloride. Wild-type C57Bl/6 mice develop arterial occlusion within 5 to 10 minutes, while fXII-deficient mice are resistant to arterial occlusion. Infusion of human fXII into fXII-deficient mice restores the wild-type phenotype. AB042 prevented thrombus formation in mice reconstituted with human fXII, while AB043 reduced the rate of thrombotic occlusion by 50%. AB042 was also tested in a baboon thrombosis model. In this model, thrombogenic collagen coated vascular grafts are inserted into a temporary arteriovenous shunt created surgically between the femoral artery and vein. Thrombus formation within the graft and downstream of the graft are followed by measuring accumulation of radio-labeled platelets and fibrin using a gamma-camera. In preliminary work, AB042 (5 mg/kg) administered intravenously prior to insertion of thrombogenic grafts effectively prevented thrombus growth down-stream of the graft, indicating a significant antithrombotic effect.

The results with the baboon model indicate that there are parallels between murine and primate physiology with regard to the fXII contribution to thrombus formation, and suggest that a fXII/fXIIa inhibitor may be an effective treatment for thrombosis in humans. In an ex vivo flow model, perfusion of human blood through collagen-coated tubes at a shear rate of 300 sec-1 results in tube occlusion by platelet and fibrin rich clot in ~15 minutes. AB042 effectively blocked fibrin formation and reduced platelet accumulation, preventing tube occlusion. AB043 was also effective at preventing clot formation, but there was evidence of some fibrin accumulation over time. These studies suggest that fXII in humans, similar to human fXII in fXII deficient mice and autologous fXII in WT baboons, contributes to pathologic thrombus growth that can lead to an occluded blood vessel.

In summary, the monoclonal anti-human fXII antibody AB042 inhibits thrombus formation in blood in vivo and ex vivo in murine, primate, and human systems by interfering with fXII activation. AB043 also has antithrombotic effects in mice, and in human blood ex vivo. These data support the hypothesis that pharmacologic inhibition of fXII activation may have therapeutic utility in disorders that are driven or aggravated by the blood contact system. Furthermore and importantly, the absence of a bleeding disorder associated with fXII deficiency strongly indicates that a treatment targeting fXII/fXIIa would be safe from the standpoint of therapy-induced bleeding risk. Drugs traditionally used for treatment or prevention of thrombosis such as platelet function inhibitors such as aspirin, clopidogrel, presugrel, anticoagulants such as heparins, low molecular weight heparins, and coumarin derivatives such as warfarin, and newer oral agents such as bivalirudin, dabigatran, rivaroxaban, activated protein C, and profibrinolytic agents, such as tissue-type plasminogen activators, urokinase, or streptokinase are associated with an increased risk of serious bleeding because they target components of the blood coagulation mechanism that are critical for normal blood coagulation (hemostasis) during injury. As fXII is dispensable for hemostasis, even its complete inhibition should not lead to increased bleeding. In support of this is the observation that mice lacking fXII, or baboons treated with AB042, do not bleed excessively during surgery or do not show abnormal bleeding when tested for hemostasis function.

Example 4

Materials and Methods

Proteins.

Human fXII, fXIIa, fXI, fXIa, PK, and high molecular weight kininogen (HK) were purchased from Enzyme Research Laboratories.

Anti-fXII Monoclonal Antibodies.

The murine fXII null genotype (C57Bl/6 background) (Kleinschnitz et al., 2006) was crossed onto the Balb-C backcrossed through seven generations. FXII-deficient Balb-C mice were immunized with human fXII, and hybridomas were generated by standard methods. Antibodies were tested for capacity to recognize human fXII by ELISA and Western blot, and to prolong the activated partial thromboplastin time (aPTT) of human plasma. Clones 9A2 and 15H8 were subcloned by limiting dilution, expanded in a CL1000 bioreactor (Integra Biosciences), and purified by cation exchange and thiophilic agarose chromatography.

Expression of Recombinant fXII and Antibody Mapping.

A human fXII cDNA was inserted into vector pJVCMV (Geng et al., 2012). Sequence encoding individual domains

TABLE 2

| HGFA Domain | Oligonucleotides for amplification of HGFA sequences. | |
|---|---|---|
| | N-terminal Oligo | C-terminal Oligo |
| EGF 1 SEQ ID NO: | 5'gatcgaattcacccgcctccaggggggcccag 21 | 5'gatcgaattcgccgcagtccttgccggtgaag 22 |
| Fibronectin I SEQ ID NO: | 5'gatcgaattcaaatgctttgatgagacccg 23 | 5'gatcgaattcgccttcgcaccaggtccgg 24 |

TABLE 2-continued

Oligonucleotides for amplification of HGFA sequences.

| HGFA Domain | N-terminal Oligo | C-terminal Oligo |
|---|---|---|
| EGF 2<br>SEQ ID NO: | 5'gatc<u>gaattc</u>catacagcttgtctgagcagc<br>25 | 5'gatc<u>gaattc</u>gatgttgcagagccgtccagcg<br>26 |
| Kringle<br>SEQ ID NO: | 5'gatc<u>gaattc</u>gatgagcgctgcttcttggg3'<br>27 | 5'gatc<u>gaattc</u>gcaggcctccaggcggcag3'<br>28 |
| Proline Rich<br>SEQ ID NO: | 5'gatc<u>gaattc</u>ctcaccagagtccaactg3'<br>29 | 5'gatc<u>gaattc</u>ggcctggcgccccggggag3'<br>30 |

Figure 10:
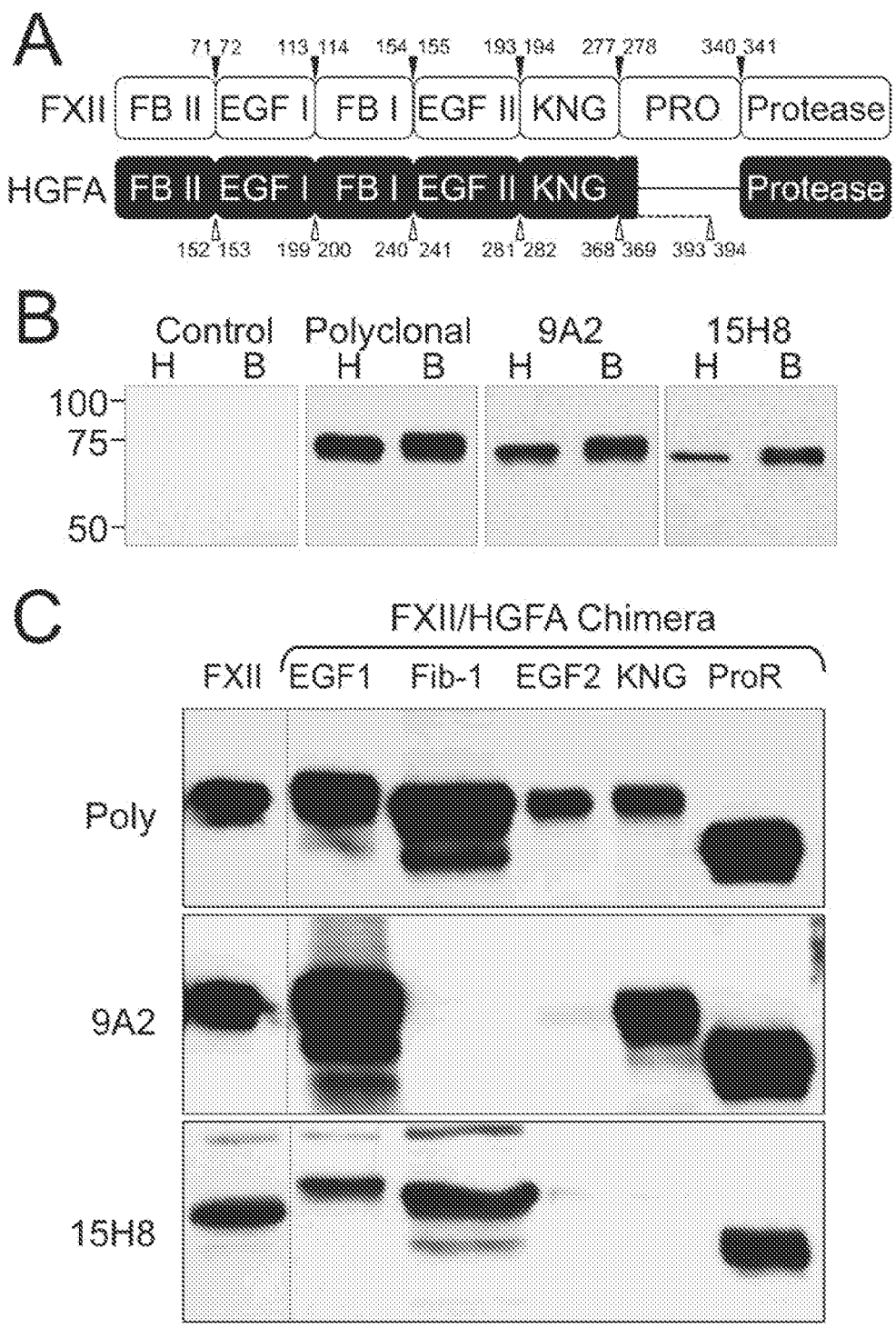
FIGS. 10A-C. Antibodies to human factor XII.

Shown are oligonucleotides used to amplify sequence from the human HGFA cDNA (Miyazawa et al., 1993).
Underlined sequences are EcoR1 restriction sites introduced onto the ends of amplified sequences so that they
can be introduced into the FXII cDNA.

from the fXII homolog hepatocyte growth factor activator (HGFA) were amplified from the human HGFA cDNA by PCR (Miyazawa et al., 1993), and used to replace corresponding sequence in the fXII cDNA (FIG. 10A, and Tables 2 and 3). HEK293 fibroblasts (ATCC-CRL1573) were transfected with pJVCMV/fXII-HGFA constructs as described (Geng et al., 2012). Conditioned serum-free medias (Cellgro Complete, Mediatech) from expressing clones were size fractionated on 10% polyacylamide-SDS gels, and chemi-luminescent Western blots were prepared using 9A2, 15H8, or goat polyclonal-anti human fXII IgG for detection.

Table 2- Oligonucleotides for amplification of HGFA sequences.

Shown are oligonucleotides used to amplify sequence from the human HGFA cDNA (Miyazawa et at., 1993). Underlined sequences are EcoRI restriction sites intnHiuced onto the ends of amplified sequences so that they can be introduced into the FXII cDNA.

TABLE 3

Oligonucleotides for restoring FXII and HGFA residues at the N- and C-terminii of inserted domains in FXII/HGFA chimeras

| HGFA Domain | Domain Terminus | Oligonucleotides |
|---|---|---|
| EGF1 | N | 5'ggggatactgttt<u>ggaaccc</u>accccgcctccaggg<br>  cccctatgacaaac<u>cttggg</u>tggggcggaggtccc 5'<br>5'- SEQ ID NO: 31<br>      SEQ ID NO: 32 - 5' |
|  | C | 5'ggcaaggactgcggc<u>accgag</u>aagtgctttgagcctcag<br>  ccgttcctgacgccg<u>tggctc</u>ttcacgaaactcggagtc 5'<br>5'- SEQ ID NO: 33<br>      SEQ ID NO: 34 - 5' |
| Fibronectin I | N | 5'ggaacccactgccag<u>aaagag</u>aaatgctttgatgag<br>  cctttggtgacggt<u>ctttctc</u>tttacgaaactactc 5'<br>5'- SEQ ID NO: 35<br>      SEQ ID NO: 36 - 5' |
|  | C | 5'ggacctggtgcgaaggc<u>acagcc</u>agccaggcctgccg<br>  cctggaccacgcttccg<u>tgtcgg</u>tcggtccggacggc 5'<br>5'- SEQ ID NO: 37<br>      SEQ ID NO: 38 - 5' |
| EGF 2 | N | 5'gcccactgccagcgg<u>ctaagg</u>catacagcttgtctg<br>  cgggtgacggtcgcc<u>gattcc</u>gtatgtcgaacagac 5'<br>5'- SEQ ID NO: 39<br>      SEQ ID NO: 40 - 5' |
|  | C | 5'ggctctgcaacatc<u>gaaacc</u>aaggcaagctgctatg<br>  ccgagacgttgtag<u>ctttgg</u>ttccgttcgacgatac 5'<br>5'- SEQ ID NO: 41<br>      SEQ ID NO: 42 - 5' |
| Kringle | N | 5'gccttctgcgacgtg<u>gatacc</u>gtggagcgctgcttcttg<br>  cggaagacgctgcac<u>ctatgg</u>ctactcgcgacgaagaac 5'<br>5'- SEQ ID NO: 43<br>      SEQ ID NO: 44 - 5' |
|  | C | 5' cgcctggaggcctgc<u>gaaaccc</u>caaccaggcggcgc<br>     gcggacctccggacg<u>ctttgggg</u>ttgggtccgccgcg 5'<br>5'- SEQ ID NO: 45<br>      SEQ ID NO: 46 - 5' |
| Proline Rich | C | 5'gacctggcacagtgc<u>caatccc</u>tcaccagagtccaactg<br>  ctggaccgtgtcacg<u>gttaggg</u>agtggtctcaggttgac 5'<br>5'- SEQ ID NO: 47<br>      SEQ ID NO: 48 - 5' |
|  | N | 5' ccggggcgccaggcc<u>tgtggc</u>cagcggctccgcaagagtc<br>     ggccccgcggtccgga<u>caccgg</u>tcgccgaggcgttctcag 5' |

TABLE 3-continued

Oligonucleotides for restoring FXII and HGFA residues at the N- and C-
terminii of inserted domains in FXII/HGFA chimeras

| HGFA Domain | Domain Terminus | Oligonucleotides |
|---|---|---|
| | | 5'- SEQ ID NO: 49<br>SEQ ID NO: 50 - 5' |

Shown are oligonucleotides used to introduce a FXII and an HGFA residue at the N-terminus of an inserted HGFA domain, and an HGFA and FXII amino acid at the C-terminus of the inserted domain. Underlined sequence indicates location of amino acids changes.

cDNA Preparation. Complementary cDNAs for recombinant FXII/HGFA chimeric proteins were prepared as follows. Initially FXII cDNAs in pCDNA3 were prepared in which individual domains were removed between the amino acid pairs shown in FIG. 10A. For example, a FXII cDNA in which the coding sequence for the EGF1 domain is deleted would be missing sequence encoding residues 72 to 113. The triplet codons for residues 71 and 114, which are now adjacent to each other, were changed to gaa and ttc, respectively. This results in an EcoR1 site (gaattc) being created at the site of the deleted domain sequence.

Sequencing.

Sequence encoding individual domains from HGFA were amplified by PCR using the oligonucleotides listed in Table 2. The oligonucleotides introduce EcoR1 sites on the ends of the amplified sequences. Amplified HGFA sequences and domain deleted FXII cDNA constructs were digested with EcoR1. The sequence from HGFA corresponding to the missing domain sequence in the FXII cDNA was ligated into the FXII cDNA, and sequenced to assure proper orientation. The resulting chimeric cDNAs have EcoR1 sites at each end of the inserted HGFA domain sequence. The gaattc sequence for the EcoR1 restriction sites were changed by site-directed mutatgenesis using a Chameleon Double-Stranded Site-Directed Mutagenesis Kit (Stratagene) so that the two amino acids encoded by gaattc are changed to the corresponding amino acids for FXII and HGFA at the N-terminus of the inserted domain, and HGFA and FXII at the C-terminus. The changes were generated using the oligonucleotides listed in Table 3.

Clotting Assays.

aPTT assays were performed by mixing 65 µL normal plasma (0.32% sodium citrate w/v) with an equal volume of PBS with or without 8 µM anti-fXII IgG. After five min at RT, 65 µL PTT-A reagent (Diagnostica Stago) was added, followed by 5 min incubation at 37° C. CaCl$_2$ (25 mM-65 µL) was added and time to clot formation determined on an ST4 fibrometer (Diagnostica Stago). In separate assays, 65 µL fXIIa (50 nM) in PBS was incubated with an equal volume of antibody (1 µM) or vehicle for 15 min prior to addition of 65 µL plasma. CaCl$_2$ was added and time to clot formation determined.

FXII Activation.

Polyphosphate (75-100 phosphate units) was prepared by gel electrophoresis as described (Muller et al., 2009). FXII (100 nM) was incubated with PTT-A reagent (2.5% of total volume) or polyphosphate (2 µM) at 37° C. in the presence of 1 µM 9A2, 15H8, both antibodies or vehicle in reaction buffer (50 mM Tris-HCl pH 7.4, 100 mM NaCl, and 1 mg/ml polyethyene glycol 8000). At various times, aliquots were removed into Polybrene (5 µM final). FXIIa activity was identified by adding chromogenic substrate S-2302 (500 µM, Diapharma) and following changes in OD405 nm on a microplate reader. Results were compared to a control curve prepared with pure fXIIa.

PK Activation.

FXIIa (1 nM) was incubated with PK (50 nM) and HK (70 nM) in reaction buffer containing 250 µM CS-3102 (Diapharma) at RT, with or without PTT-A reagent (5% v/v), and with or without anti-fXII IgG (100 nM). Changes in OD405 nm reflecting conversion of PK to α-kallikrein were followed on a microplate reader.

Thrombin Generation.

Normal plasma (0.32% sodium citrate w/v) was supplemented with 415 µM Z-Gly-Gly-Arg-AMC, 5 µM PC/PS vesicles, and 4 µM IgG anti-fXII IgG. Supplemented plasma (40 µl) was mixed with PTT-A reagent (1% v/v). Ten microliters of 20 mM HEPES, pH 7.4, 100 mM CaCl$_2$, 6% BSA was added and fluorescence (excitation λ 390 nm, emission λ 460 nm) was monitored at 37° C. on a Thrombinoscope®.[31] In a separate experiment, fXII-deficient plasma (George King) was treated in a similar manner, except that XXX nM fXIIa was added with PTT-A reagent. Each condition was tested three times in duplicate. Peak thrombin generation and endogenous thrombin potential (ETP) were determined (Thrombinoscope Analysis software, 3.0).

Flow Model.

(Tucker et al., 2009) Blood was collected from healthy volunteers (0.32% sodium citrate w/v). Platelets were labeled by adding 1,1'-dimethyl-3,3,3',3'-tetramethylindodicarbocyanine iodide (DiICl$_5$) (2 µM). Blood was supplemented with Alexa-594 labeled fibrinogen (20 µg/ml) and 4 µM anti-fXII IgG, and incubated for 30 min at 37° C. prior to use. Glass capillary tubes (0.2×2.0×50 mm, VitroCom) were coated with 100 µg/ml type I fibrillar collagen (Chrono-Log) overnight at 4° C., then blocked with 0.5% BSA. Blood was perfused through tubes at an initial shear rate of 300 s$^{-1}$ using a syringe pump. Prior to entering the capillary tube, blood was mixed with 20 mM Tris-HCl pH 7.4, 154 mM NaCl with 37.5 mM CaCl$_2$, 19.8 mM MgCl$_2$ via a second pump and passed through a coiled 12 cm mixing tube. Blood is diluted ~20% by this step, with final free [Ca$^{2+}$] and [Mg$^{2+}$] ~2.5 and 1.2 mM, respectively. Tubes were subsequently perfused with 3.5% formaldehyde/PBS solution and imaged by laser-scanning microscopy, using a Zeiss LSM 710 microscope.

Capillary Occlusion Assay.

(Puy et al., 2013) Glass capillary tubes (0.2×2 mm, VitroCom) were incubated for 1 hr at RT with fibrillar collagen (100 µg/ml), washed with PBS, blocked with 5 mg/ml denatured BSA for 1 hr, then placed in a vertical position. The top of the tube was connected to reservoir, and the bottom was immersed in PBS. Human blood (0.32% sodium citrate w/v) supplemented with 7.5 mM CaCl$_2$ and 3.75 mM MgCl$_2$ was added to the reservoir. Blood flows through the tube under the force of gravity. The height of the sample reservoir is maintained to produce an initial shear rate of 300 s$^{-1}$.

Mouse Thrombosis Model.

FXII-deficient (fXII$^{-/-}$) C57Bl/6 mice were anesthetized with pentobarbital. PBS (100 μL) with or without 10 μg human fXII, and with or without 100 μg of anti-fXII IgG, was infused into the right jugular vein. Thrombus formation was induced in the right carotid artery by applying 3.5% ferric chloride (FeCl$_3$), as described (Cheng et al., 2010). Arterial blood flow was monitored for 30 minutes using a Doppler flow probe (Model 0.5 VB; Transonic System). Studies with mice were approved by the Institutional Animal Care and Use Committee (IACUC) of Vanderbilt University.

Baboon Thrombosis Model.

Figure 11:
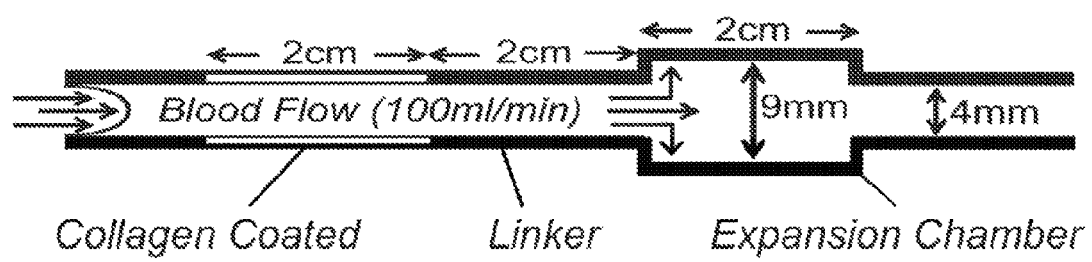
FIG. 11. Schematic diagram of the thrombogenic device used in baboons. The device is made of a 20 mm long segment of ePTFE graft tubing (4 mm diameter) coated with collagen. 20 mm downstream of the collagen-coated segment is an expansion chamber made of silicon rubber tubing (9 mm diameter, 20 mm length). The collagen coated segment and silicon expansion changer are connected by a 20 mm linker of uncoated silicon tubing (4 mm diameter).

Non-terminal studies were performed on two male baboons (*Papio anubis*) with exteriorized femoral arteriovenous shunts, as described (Cheng et al., 2010; Gruber and Hanson 2003 and Tucker et al., 2009). Thrombus formation was initiated by deploying a thrombogenic graft (FIG. 11) into the shunt for 60 min. The graft is comprised of a 20×4 mm ePTFE [Gortex] segment coated with collagen, a 20×4 mm silicon rubber linker, and a 20×9 mm silicon rubber expansion chamber. Flow through the shunt was restricted to 100 ml/min, producing an initial wall shear rate in the graft of 265 s$^{-1}$. Platelet deposition in the graft and expansion chamber was assessed in real time by quantitative imaging of $^{111}$In-labeled platelet accumulation using a GE-400T gamma scintillation camera interfaced to a NuQuest Inte-Cam computer system. Endpoint fibrin deposition was determined by direct measurement of $^{125}$I-labeled fibrinogen, as described (Cheng et al., 2010, Gruber and Hanson 2003 and Tucker et al., 2009) Plasma Thrombin-antithrombin (TAT) complex levels were measured with an Enzygnost TAT ELISA (Siemens). Studies with baboons were approved by the IACUC of Oregon Health and Sciences University.

Example 5

Results

Anti-fXII Antibodies.

Antibodies 9A2 and 15H8 recognize fXII in human and baboon plasma (FIG. 10B) on Western blots. The fXII gene arose from a duplication of the HGFA gene.[30,33] FXII and HGFA have similar domain structures, except that fXII has a proline-rich region not found in HGFA (FIG. 10A). The inventors prepared fXII proteins with individual domains replaced by corresponding HGFA domains. With the exception of the fXII/HGFA-fibronectin type II domain chimera, all proteins were secreted by a human fibroblast line (FIG. 10C, top). 9A2 and 15H8 appear to recognize distinct epitopes on fXII, with 9A2 binding to the fibronectin type I and/or EGF2 domains (FIG. 10C, middle), and 15H8 to the EGF2 and/or kringle domains (FIG. 10C, bottom).

9A2 and 15H8 prolong the aPTT of human plasma (FIG. 12A), with 15H8 having a greater effect. Antibodies at ~2 to 3-times the plasma fXII concentration achieved maximum effects. Combining 9A2 and 15H8 produced a greater degree of inhibition (FIG. 12B), consistent with the two antibodies recognizing distinct epitopes. The curve (open circles) in FIG. 12C shows the relationship between fXII concentration and the aPTT of human plasma. Using this curve for comparison, the effect of 15H8 on the aPTT of normal plasma corresponds to >95% inhibition of fXII activity, while 9A2 achieves ~50% reduction. 15H8 produced a greater degree of prolongation of the aPTT in baboon plasma (FIG. 12D) than human plasma (FIG. 12A). The curve with closed circles in FIG. 12C was prepared by mixing baboon plasma with fXII-deficient human plasma. When data in FIG. 12D are compared to this curve, it appears that 15H8 can inhibit >99% of the fXII activity in baboon plasma. 9A2 did not prolong the aPTT of baboon plasma.

Effects of Anti-fXII Antibodies on fXII and PK Activation In Vitro.

FXII undergoes autoactivation in the presence of a variety of surfaces and polymers (Muller et al., 2009, Gailani and Neff 2013 and White-Adams et al., 2010). The inventors tested the capacity of anti-fXII antibodies to inhibit fXII activation in the presence of a silica-based PTT reagent (FIG. 13A) or polyphosphate (a potential pathophysiologic fXII activator, FIG. 13B). Both antibodies reduced fXII activation with silica, with 15H8 having a greater effect, while both had roughly similar effects with polyphosphate. These findings support early work indicating that the heavy chain of fXII is required for binding to polyanions. In the absence of a polyanion neither antibody had a significant effect on fXIIa cleavage of PK (FIG. 13C), while 15H8 reduced fXI activation by fXIIa by ~50% (FIG. 13D). Mixing fXII and PK results in reciprocal activation of the two proteins, probably triggered by traces of fXIIa and α-kallikrein in the zymogen preparations. Both 9A2 and 15H8 modestly inhibit this process in the absence of a polyanion (FIG. 13E). Cumulatively, the data indicate that the inhibitory effect of 9A2 and 15H8 on the PTT assay is primarily due to inhibition of fXII activation, with perhaps a modest effect on fXI activation by fXIIa.

Effects of Anti-fXII Antibodies on Thrombin Generation in Plasma.

Addition of aPTT reagent to normal plasma leads to a burst of thrombin generation (FIG. 14A, ETP 1805 nM·min) that is almost completely blocked by 15H8. 9A2 reduces ETP by ~50% (961 nM·min), with a delay in time to peak thrombin generation. Similar results were obtained using collagen to induce coagulation (FIG. 14B), although less thrombin is generated than with aPTT reagent. In contrast, neither antibody blocks thrombin generation induced by adding fXIIa to fXII-deficient plasma supplemented with aPTT reagent (FIG. 14C). Considering these data, and those for fXII and PK activation, it appears that 15H8 and 9A2 produce their effects on the aPTT largely by inhibiting conversion of fXII to fXIIa. 15H8 may also have some effect on PK activation by fXIIa, while neither antibody affects surface-dependent fXI activation by fXIIa in plasma appreciably.

Anti-fXII Antibodies in Flow Models.

Previously, the inventors showed that anti-fXI antibodies inhibit fibrin formation in recalcified human blood perfused across collagen-coated surfaces (Tucker et al., 2009) FIG. 15A shows images from collagen-coated tubes perfused with human blood at a shear rate of 300 sec$^{-1}$. Platelet aggregates appear green and fibrin strands orange. The anti-fXI antibody 01A6 (Tucker et al., 2009) blocks fibrin generation in this system. 9A2 and 15H8 also substantially reduce fibrin deposition, although some fibrin does form. These data indicate that the anti-fXII antibodies have an effect in flowing human blood that is similar to the effect previously reported for anti-fXI antibodies (Tucker et al., 2009) 9A2 and 15H8 also prolonged the time it takes for whole blood to occlude a collagen-coated capillary tube in which flow is induced by gravity (FIG. 15B). At a concentration (1.3 μM) ~3.5 fold higher than the plasma fXII concentration, 9A2 increased time to occlusion 2-fold, while 15H8 increased it nearly 3-fold.

Anti-IXII Antibodies in a Murine Thrombosis Model.

Exposing blood vessels in mice to concentrated $FeCl_3$ results in changes to the blood vessel endothelium that lead to thrombus formation in a fXII- and fXI-dependent manner (Renne et al., 2005, Cheng et al., 2010 and Barr et al., 2013) FXII-deficient C57Bl/6 mice are uniformally resistant to carotid artery occlusion induced by 3.5% $FeCl_3$, while wild type C57Bl/6 mice reproducibly develop occlusion in 10-15 minutes (Cheng et al., 2010). Infusing human fXII into fXII-deficient animals to restore the plasma fXII level to ~20% of normal restores the wild type phenotype (n=5, all mice with vessel occlusion). Co-administration of fXII and a 10-fold molar excess of 9A2 reduced the incidence of arterial occlusion by 50%, while 15H8 prevented arterial occlusion (n=6 for each antibody).

Anti-IXII Antibodies in a Baboon Thrombosis Model.

The inventors tested the effects of 15H8 on platelet (FIG. 16A) and fibrin (FIG. 16B) deposition in thrombogenic devices (FIG. 11) deployed into arteriovenous shunts in baboons. Thrombus formation is triggered by the collagen-coated segment of the graft where the initial wall shear rates is ~265 $sec^{-1}$. A distal expansion chamber made of silicon rubber is incorporated to assess thrombus formation under lower shear (<30 $sec^{-1}$, FIG. 11). 15H8 (5-6 mg/kg IV) prolonged the aPTT from 29.5 to 50 seconds in one baboon, and from 33.5 to 78 seconds in a second animal Based on the curve in FIG. 12C (black circles), these results suggest substantial (~99%) inhibition of fXII activity. The inhibitory effect lasted >24 hrs. Results were obtained for nine thrombogenic devices prior to 15H8 administration (controls), and four devices after 15H8 administration. 15H8 did not affect platelet deposition (FIG. 16A) within the collagen-coated graft, had a modest effect in the linker region down-stream from the collagen, and caused a substantial (~80% reduction compared to control) in the expansion chamber. 15H8 reduced fibrin deposition by 70±5% in the collagen-coated portion of the graft (FIG. 16B, left panel), and by 95±1% in the linker-expansion chamber (FIG. 16B, right panel). The grafts promote thrombin generation that can be detected in the systemic circulation by measuring TAT complex (Tucker et al., 2009 and Gailani and Neff 2013) 15H8 reduced TAT levels in the systemic circulation by ~50% (FIG. 16C).

Example 6

Discussion

Anticoagulants currently used for treatment or prevention of thromboembolism directly inhibit thrombin or factor Xa activity, or limit production of their precursors. While effective, this strategy increases bleeding risk because the targeted proteases are central to hemostasis. This places limits on the types of patients who can safely be treated with anticoagulants, and the clinical scenarios in which treatment is applied. The intuitive notion that thrombosis reflects "hemostasis in the wrong place" has been brought into question by data from rodent models demonstrating pro-thrombotic roles for the proteases fXIa and fXIIa (Wang et al., 2006, Renne et al., 2005, Cheng et al., 2010, Muller et al., 2009, Kleinschnitz et al., 2006, Colman 2006, Hagedorn et al., 2010 and Chen et al., 2012). These observations suggest that it may be possible to develop therapies in which antithrombotic effects are largely or completely dissociated from anti-hemostatic effects.

Both fXIa and fXIIa have features that make them attractive therapeutic targets. There is substantial evidence supporting a role for fXI in human thrombosis. Plasma fXI levels at the upper end of the normal range increase risk for MI (Doggen et al., 2006), stroke (Suri et al., 2010) and venous thromboembolism (VTE) (Meijers et al., 2000 and Cushman et al., 2009) relative to the remainder of the population, while severe fXI deficiency reduces incidence of stroke (Salomon et al., 2008) and VTE (Salomon et al., 2011). The major function of fXIa, activation of factor IX, appears to serve a limited role in hemostasis, primarily directed at preventing excessive trauma-induced bleeding in tissues with high fibrinolytic activity such as the oropharynx and urinary tract (Gailani and Neff 2013 and Seligsohn 2009). In patients with severe fXI deficiency some types of surgery (Salomon et al., 2006) and normal child birth (Salomon et al., 2005) are associated with relatively low rates of excessive bleeding in the absence of factor replacement. Indeed, many fXI-deficient individuals do not experience abnormal hemostasis, and symptomatic patients rarely bleed spontaneously (with the exception of menorrhagia) (Gailani and Neff 2013 and Seligsohn 2009) indicating that drugs targeting fXIa would be associated with less bleeding than drugs that inhibit thrombin or factor Xa. The absence of a bleeding diathesis in fXII-deficient individuals suggests that drugs specifically targeting this protein would not compromise hemostasis, allowing them to be used in patients with the most restrictive contra-indications for current anticoagulation therapies. Enthusiasm for developing fXIIa inhibitors, however, is tempered by two considerations. First, while numerous functions are attributed to fXIIa, the physiologic roles of the protease are incompletely understood. Perhaps as important, a clear link between fXII and thrombosis in humans is not established.

Anecdotal reports suggesting that fXII deficiency actually predisposes to VTE date back to the death of the first person identified with severe fXII deficiency from a pulmonary embolism (Ratnoff 1985). Subsequent investigations did not confirm an association between low fXII levels and VTE (Koster et al., 1994 and Zeerleder et al., 1999) and an analysis of case reports concluded that most thrombotic events in fXII-deficient patients are unrelated to the deficiency (Girolami et al., 2004). However, two recent studies have returned the issue of fXII levels and thrombotic risk to the forefront. Doggen et al. reported an inverse relationship between plasma fXII levels and risk of myocardial infarction (Doggen et al., 2006), with an odds ratio of 0.4 for individuals in the highest quartile for fXII levels compared to those in the lowest quartile. This study examined fXII levels within the broad normal range, and not the consequences of severe fXII deficiency, which may be more relevant for anticipating effects of therapeutic fXII inhibition. Endler et al. also observed an inverse relationship between plasma fXII and all cause mortality (Endler et al., 207), with participants with 10-20% of the normal fXII level having a hazard ratio of 4.7 compared to those with fXII levels >100% of normal. Curiously, there was no significant increase in mortality for subjects with fXII levels in the 1-10% of normal range, suggesting a fundamental difference between severe and moderate fXII deficiency. Data from the studies from (Doggen et al. and Endler et al.) seem at odds with work showing that elevated plasma fXIIa levels correlate with risk of coronary events (Grundt et al., 2004 and Siegerink et al., 2010). While it is difficult to draw unifying conclusions from this conflicting data, there seems to be grounds for concern that fXII may not contribute to thrombosis in humans in the same manner that it contributes to thrombosis in the mouse models.

The current study was designed to examine the contribution of fXII in human/primate models known to require factor XI for normal thrombus formation. The antibodies 9A2 and 15H8 recognize epitopes on the non-enzymatic heavy chain region of fXII. These antibodies reduce fXII activity in plasma exposed to an activator of contact activation primarily by inhibiting fXII activation, and not fXIIa activity. This supports work showing the fXII heavy chain is required for binding to polyanions, a key step in surface-dependent fXII activation (Pixley et al., 1987, Clarke et al., 1989 and Citarella et al., 2000). In baboons, 15H8 reduce fibrin deposition in a collage-coated thrombogenic graft, and limited platelet-rich thrombus growth under low shear. It is illustrative to compare this performance to those of anti-fXI antibodies in the same model. The anti-fXI antibody O1A6 is a potent inhibitor of factor IX activation by fXIa, and interferes with fXI activation by fXIIa (Tucker et al, 2009 and Geng et al., 2012). O1A6 significantly reduces platelet and fibrin accumulation within the collagen-coated segments of grafts, and reduces systemic and local TAT levels by ≥80%, indicating a profound effect on thrombin generation. Platelets adhere to collagen in the presence of O1A6, but there is a marked defect in three-dimensional thrombus growth (Tucker et al., 2009), consistent with the thrombus instability observed in fXI and fXII deficient mice (Rene et al., 2005 and Cheng et al., 2010). In vitro, the anti-fXI antibody 14E11 inhibits fXI activation by fXIIa, but does not affect fXIa activity (Cheng et al., 2010). In baboons, similar to 15H8, 14E11 had relatively little effect on platelet accumulation within the collagen-coated segment of the graft, but had a comparable effect to 15H8 in limiting downstream platelet deposition. The results with human blood in a collagen-based flow system are, in general, consistent with those for the primate model. Taken as a whole, the data suggest that 15H8 reduces the rate of thrombin generation induced by exposing blood to collagen, resulting in decreased fibrin deposition and a more modest decrease in platelet accumulation. The antithrombotic effect is not as great as the one produced by O1A6. Interestingly, O1A6 (Tucker et al., 2009), 14E11 (Cheng et al, 2010) and 15H8 prolonged the aPTT to similar extents in treated baboons, demonstrating that it is the mechanism targeted, and not the absolute value of the aPTT that correlates with the antithrombotic effect.

The published results with the baboon model (Cheng et al., and Tucker et al., 2009) and the current study raise the possibility that inhibition of fXII in humans may produce a less potent antithrombotic effect than inhibition of fXI. In comparison, fXII deficient mice are somewhat more resistant to thrombotic occlusion of the carotid artery than are fXI deficient mice after $FeCl_3$ or laser injury to the vessel (Cheng et al., 2010). Thrombin-mediated feedback activation of fXI may explain the observation that fXII deficiency does not cause a hemorrhagic tendency. Perhaps this mechanism plays a more prominent role in thrombus formation in primates than in mice, accounting for the lower effectiveness of 15H8 (and 14E11) compared to O1A6. This scenario is consistent with the more modest reduction in TAT levels in baboons treated with 15H8 compared to O1A6 (Tucker et al., 2009). Alternatively, it appears that relatively small amounts of fXII have significant effects on the aPTT in baboon and human plasmas, suggesting that it may be difficult to inhibit this protein sufficiently with an antibody to negate its prothrombotic effect. Indeed, while 15H8 substantially reduced fXII activity in the aPTT, it did not block it completely. This explanation would be consistent with results reported by Pixley and co-workers showing that an antibody that neutralized ~60% of the fXII activity in baboon blood did not affect endotoxin-induced disseminated intravascular coagulation (Pixley et al., 1993). In comparison, modestly reducing fXI levels in baboons by as little as 50%, reduced thrombus formation in the arteriovenous shunt model (Crosby et al., 2013). Furthermore, inhibiting fXII activity with an antibody to produce a similar effect to total fXII deficiency is made difficult by the relatively high plasma fXII concentration (400 nM) compared to fXI (30 nM). These observations have implications for developing therapeutic fXII/XIIa inhibitors, which may need to inhibit a high percentage of protease activity to produce a therapeutic effect.

The results presented here demonstrate that fXIIa contributes to thrombus growth in primate blood in vivo and ex vivo, and support the premise that fXIIa inhibition may be useful for treating or preventing thrombosis in humans. However, it may be more difficult to generate a potent antithrombotic effect with a fXIIa inhibitor than with a fXIa inhibitor, because of the higher degree of inhibition required. The data from recent epidemiologic studies showing an inverse relationship between fXII levels and cardiovascular disease also raise questions about the long term effects of fXII inhibition in humans that need to be considered when selecting potential targets for novel antithrombotic drugs.

All of the compositions and/or methods disclosed and claimed herein can be made and executed without undue experimentation in light of the present disclosure. While the compositions and methods have been described in terms of specific embodiments, it will be apparent to those of skill in the art that variations can be applied to the compositions and/or methods and in the steps or in the sequence of steps of the method described herein without departing from the concept, spirit and scope of the disclosure. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept as defined by the appended claims.

VIII. References

The following references, to the extent that they provide exemplary procedural or other details supplementary to those set forth herein, are specifically incorporated herein by reference:

Atherton et al., Biol Reprod. 32(1):155-71 1985.
Barr et al., Blood.; 121(18):3733-3741, 2013.
Bird et al., Science 242:423-426, 1988.
Blat & Seiffert, Thromb. Haemost. 99:457-460, 2008.
Blat et al., Thromb. Haemost. 99:457-460, 2008.
Broze et al., Biochemistry 29:7539-7546, 1990.
Brunnee et al., Blood 81:580-586, 1993.
Capaldi et al., Biochem. Biophys. Res. Comm., 76:425, 1977.
Cawthern et al., Blood 91:4581-4592, 1998.
Chen et al., JACC Cardiovasc Imaging.; 5(11):1127-1138, 2012.
Cheng et al., Blood.; 116(19):3981-3989, 2010.
Clarke et al., J Biol Chem.; 264(19):11497-11502.
Citarella et al., Thromb Haemost; 84(6):1057-1065.
Colman, J Ex Med.; 203(3):493-495, 2006.
Crosby et al., Arterioscler Thromb Vasc Biol.; 33(7):1670-1678, 2013.
Cushman et al., Blood.; 114(14):2878-2883, 2009.
Davie et al., Biochemistry 30:10363-10370, 1991.
Dholakia et al., J Biol Chem. 264(34):20638-42, 1989.

Doggen et al., Blood.; 108(13):4045-4051, 2006.
Doolittle and Ben-Zeev, Methods Mol Biol. 109:215-37, 1999.
Endler et al., J Thromb Haemost.; 5(6):1143-1148, 2007.
Furie et al., Hematology: Basic Principles and Practice, 4th ed. New York: Churchill Livingstone 1931, 2005.
Gailani and Broze, Metabolic and Molecular Basis of Inherited Disease, Scriver et al., eds., New York, N.Y.: McGraw-Hill, pages 4433-4453, 2001.
Gailani and Neff, Hematology, Basic Principles and Practice, 6th edition., Philadelphia, pp 1971-1986, 2013.
Gailani et al., Science 253:909-912, 1991.
Geng et al., J Biol Chem.; 287(45):38200-38209, 2012.
Ghanem et al., J. Vet. Med. Sci. 67:713-715, 2005.
Girolami, et al., J Thromb Thrombolysis.; 17(2):139-143, 2004.
Gruber and Hanson, Blood.; 102(3):953-955, 2003.
Gruber and Hanson, Curr. Pharm. Des. 9(28):2367-2374, 2003.
Grundt et al., Am Heart J.; 147(2):260-266, 2004.
Gulbis and Galand, Hum Pathol. 24(12):1271-85, 1993.
Hagedorn et al., Circulation.; 121(13):1510-1517, 2010.
Higgins et al., Computer Applications in the Biosciences (CABIOS), 8(2): 189-191), 1992.
Huston et al., Proc. Natl. Acad. Sci. USA 85:5879-5883, 1988.
Ill et al., Protein Eng 10:949-57, 1997.
Keularts et al., Thromb. Haemost. 85:1060-1065, 2001.
Khatoon et al., Prog Clin Biol Res. 317:801-7, 1989.
Kleinschnitz et al., J Exp Med., 203(3):513-518, 2006.
Knowler et al., J. Am. Vet. Med. Assoc. 205:1557-61, 1994.
Koster et al., Br J Haematol.; 87(2):422-424, 1994.
Meijers et al., N Engl J Med.; 342(10):696-701, 2000.
Miyazawa et al., J Biol Chem.; 268(14):10024-10028, 1993.
Müller et al., Cell.; 139(6):1143-1156, 2009.
Naito et al., J. Biol. Chem. 266:7353-7358, 1991.
Oliver et al., Arterioscler. Thromb. Vasc. Biol. 19:170-177, 1999.
Owens & Haley, Biochem Biophys Res Commun 142(3): 964-71, 1987
Pedicord et al., Proc. Natl. Acad. Sci. U.S.A. 104:12855-12860, 2007.
Pixley et al., J Clin Invest.; 91(1):61-68, 1993.
Ponczek et al., J Thromb Haemost; 6(11):1876-1883, 2008.
Potter & Haley, Methods Enzymol. 1983; 91:613-33, 1983
Puy et al., J Thomb Haemost; 11(7):1341-1352, 2013.
Ratnoff, TransAssoc AmPhysicians.; 98:151-161, 1985.
Remington's Pharmaceutical Sciences, 15th Ed. Mack Printing Company, 1975.
Remington's Pharmaceutical Sciences, 18th Ed. Mack Printing Company, 1990.
Renne et al., Expert Rev. Cardiovasc. Ther. 5:733-741, 2007.
Salomon et al., Blood Coagul Fibrinolysis.; 16(1):37-41, 2005.
Salomon et al., Blood.; 111(18):4113-4117, 2008.
Salomon et al., Haemophilia.; 12(5):490-493, 2006.
Salomon et al., Thromb. Haemost.; 105(2):269-273, 2011.
Seligsohn et al., Thromb. Haemost. 98:84-89, 2007.
Seligsohn, J Thromb Haemost.; 7(Suppl1):84-87, 2009.
Siegerink et al., Circulation.; 122(18):1854-1861, 2010.
Suri et al., Cerebrovasc Dis.; 29(5):497-502, 2010.
Thompson et al., Nucleic Acids Res, 2(22): 4673-4680, 1994.
Troxel et al., J. Am. Anim. Hosp. Assoc. 38:549-553, 2002.
Tucker et al., Blood.; 113(4):936-944, 2009.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 4,472,509
U.S. Pat. No. 4,680,338
U.S. Pat. No. 4,938,948
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,856,456
U.S. Pat. No. 5,880,270
von dem Borne et al., Blood 86:3035-3042, 1995.
von dem Borne et al., J. Clin. Invest. 99:2323-2327, 1997.
von dem Borne et al., Thromb. Haemost. 78:834-839, 1997.
Wang et al., J Thromb Haemost.; 3(4):695-702, 2006.
Ward et al., Nature 341:544-546, 1989.
Wawrzynczak & Thorpe, Cancer Res. 15; 47(22):5924-311987a.
Wawrzynczak & Thorpe, J Natl Cancer Inst. 79(5):1101-12, 1987b.
White-Adams et al., J Thromb Haemost.; 8(6):1295-1301, 2010.
Wielders et al., Arterioscler. Thromb. Vasc. Biol. 24:1138-1142, 2004.
Wu and Kabat, J Exp Med. 1; 132(2):211, 1970.
Wu et al., Proc Natl Acad Sci USA. 72(12):5107, 1975.
Zeerleder et al., Thromb Haemost.; 82(4):1240-1246, 1999.

What is claimed is:

1. An antibody which binds factor XII comprising:
   (a) a light chain comprising light chain CDRs represented by SEQ ID NOS: 1, 2 and 3; and
   (b) a heavy chain comprising heavy chain CDRs represented by SEQ ID NOS: 4, 5 and 6.

2. The antibody of claim 1, wherein the light chain framework regions are represented by SEQ ID NOS: 7, 8, 9 and 10, or having 5 or fewer conservative amino acid substitutions.

3. The antibody of claim 1, wherein the heavy chain framework regions are represented by SEQ ID NOS: 11, 12, 13 and 14, or having 5 or fewer conservative amino acid substitutions.

4. The antibody of claim 1, wherein the light chain is represented by SEQ ID NO: 15.

5. The antibody of claim 4, wherein the light chain leader sequence is represented by SEQ ID NO: 16.

6. The antibody of claim 4, wherein said light chain is encoded by a nucleic acid represented by SEQ ID NO: 19.

7. The antibody of claim 1, wherein the heavy chain is represented by SEQ ID NO: 17.

8. The antibody of claim 1, wherein the heavy chain leader sequence is represented by SEQ ID NO: 18.

9. The antibody of claim 7, wherein the heavy chain is encoded by a nucleic acid represented by SEQ ID NO: 20.

10. The antibody of claim 1, wherein the antibody is a single-chain antibody.

11. The antibody of claim 1, wherein the antibody is an antibody fragment.

12. The antibody of claim 9, wherein the antibody fragment is further defined as Fab', Fab, F(ab')$_2$, Fv, scFv, or bivalent antibody.

13. A cell or cell line comprising a nucleic acid encoding an antibody which binds factor XII comprising:
   (a) a light chain comprising light chain CDRs represented by SEQ ID NOS: 1, 2 and 3; and
   (b) a heavy chain comprising heavy chain CDRs represented by SEQ ID NOS: 4, 5 and 6.

14. The cell or cell line of claim 13, wherein the light chain framework regions are represented by SEQ ID NOS: 7, 8, 9 and 10, or having 5 or fewer conservative amino acid substitutions.

15. The cell or cell line of claim 13, wherein the heavy chain framework regions are represented by SEQ ID NOS: 11, 12, 13 and 14, or having 5 or fewer conservative amino acid substitutions.

16. The cell or cell line of claim 13, wherein the light chain is represented by SEQ ID NO: 15.

17. The cell or cell line of claim 13, wherein the heavy chain is represented by SEQ ID NO: 17.

18. A method of inhibiting activation of factor XII comprising contacting unactivated factor XII with an antibody which binds factor XII comprising:
   (a) a light chain comprising light chain CDRs represented by SEQ ID NOS: 1, 2 and 3; and
   (b) a heavy chain comprising heavy chain CDRs represented by SEQ ID NOS: 4, 5 and 6.

19. The method of claim 18, wherein factor XII is located in a subject.

20. A method of modulating thrombosis and/or treating pathologic hypercoagulation involving activation of factor XII in a subject comprising administering an effective amount of an antibody which binds factor XII comprising:
   (a) a light chain comprising light chain CDRs represented by SEQ ID NOS: 1, 2 and 3; and
   (b) a heavy chain comprising heavy chain CDRs represented by SEQ ID NOS: 4, 5 and 6.

* * * * *

SEQUENCE LISTING

<160> NUMBER OF SEQ ID NOS: 50

<210> SEQ ID NO 1
<211> LENGTH: 16
<212> TYPE: PRT
<213> ORGANISM: Artificial
<220> FEATURE:
<223> OTHER INFORMATION: Synthetic peptide

<400> SEQUENCE: 1

Arg Ser Ser Lys Ser Leu Leu His Ser Asn Gly Ile Thr Tyr Leu Tyr
 1               5                  10                  15

```
<210> SEQ ID NO 2
<211> LENGTH: 7
<212> TYPE: PRT
<213> ORGANISM: Artificial
<220> FEATURE:
<223> OTHER INFORMATION: Synthetic peptide

<400> SEQUENCE: 2

Tyr Met Ser Asn Leu Ala Ser
1               5

<210> SEQ ID NO 3
<211> LENGTH: 9
<212> TYPE: PRT
<213> ORGANISM: Artificial
<220> FEATURE:
<223> OTHER INFORMATION: Synthetic peptide

<400> SEQUENCE: 3

Met Gln Ser Leu Glu Tyr Pro Tyr Thr
1               5

<210> SEQ ID NO 4
<211> LENGTH: 23
<212> TYPE: PRT
<213> ORGANISM: Artificial
<220> FEATURE:
<223> OTHER INFORMATION: Synthetic peptide

<400> SEQUENCE: 4

Asp Ile Val Met Thr Gln Ala Thr Pro Ser Val Pro Val Thr Pro Gly
1               5                   10                  15

Glu Ser Val Ser Ile Ser Cys
            20

<210> SEQ ID NO 5
<211> LENGTH: 15
<212> TYPE: PRT
<213> ORGANISM: Artificial
<220> FEATURE:
<223> OTHER INFORMATION: Synthetic peptide

<400> SEQUENCE: 5

Trp Phe Leu Gln Arg Pro Gly Gln Ser Pro Gln Arg Leu Ile Tyr
1               5                   10                  15

<210> SEQ ID NO 6
<211> LENGTH: 32
<212> TYPE: PRT
<213> ORGANISM: Artificial
<220> FEATURE:
<223> OTHER INFORMATION: Synthetic peptide

<400> SEQUENCE: 6

Gly Val Pro Asp Arg Phe Ser Gly Arg Gly Ser Gly Thr Asp Phe Thr
1               5                   10                  15

Leu Arg Ile Ser Arg Val Glu Ala Glu Asp Val Gly Val Tyr Tyr Cys
            20                  25                  30

<210> SEQ ID NO 7
<211> LENGTH: 10
<212> TYPE: PRT
<213> ORGANISM: Artificial
<220> FEATURE:
<223> OTHER INFORMATION: Synthetic peptide

<400> SEQUENCE: 7
```

Phe Gly Gly Gly Thr Lys Leu Glu Ile Lys
1               5                   10

<210> SEQ ID NO 8
<211> LENGTH: 10
<212> TYPE: PRT
<213> ORGANISM: Artificial
<220> FEATURE:
<223> OTHER INFORMATION: Synthetic peptide

<400> SEQUENCE: 8

Gly Phe Asn Ile Lys Asp Asp Tyr Met His
1               5                   10

<210> SEQ ID NO 9
<211> LENGTH: 17
<212> TYPE: PRT
<213> ORGANISM: Artificial
<220> FEATURE:
<223> OTHER INFORMATION: Synthetic peptide

<400> SEQUENCE: 9

Trp Ile Asp Pro Glu Asn Gly Asp Thr Glu Tyr Ala Ser Lys Phe Gln
1               5                   10                  15

Gly

<210> SEQ ID NO 10
<211> LENGTH: 10
<212> TYPE: PRT
<213> ORGANISM: Artificial
<220> FEATURE:
<223> OTHER INFORMATION: Synthetic peptide

<400> SEQUENCE: 10

Asn Tyr Tyr Gly Ser Ser Phe Phe Ala Tyr
1               5                   10

<210> SEQ ID NO 11
<211> LENGTH: 25
<212> TYPE: PRT
<213> ORGANISM: Artificial
<220> FEATURE:
<223> OTHER INFORMATION: Synthetic peptide

<400> SEQUENCE: 11

Glu Val Gln Leu Gln Gln Ser Gly Ala Glu Leu Val Arg Pro Gly Ala
1               5                   10                  15

Ser Val Lys Leu Ser Cys Thr Ala Ser
            20                  25

<210> SEQ ID NO 12
<211> LENGTH: 14
<212> TYPE: PRT
<213> ORGANISM: Artificial
<220> FEATURE:
<223> OTHER INFORMATION: Synthetic peptide

<400> SEQUENCE: 12

Trp Val Lys Gln Arg Pro Glu Gln Gly Leu Glu Trp Ile Gly
1               5                   10

<210> SEQ ID NO 13
<211> LENGTH: 32
<212> TYPE: PRT
<213> ORGANISM: Artificial

-continued

```
<220> FEATURE:
<223> OTHER INFORMATION: Synthetic peptide

<400> SEQUENCE: 13

Lys Ala Thr Ile Thr Ser Asp Thr Ser Ser Asn Thr Ala Tyr Leu Gln
1               5                   10                  15

Leu Ser Ser Leu Thr Ser Glu Asp Thr Ala Val Tyr Tyr Cys Thr Glu
            20                  25                  30

<210> SEQ ID NO 14
<211> LENGTH: 11
<212> TYPE: PRT
<213> ORGANISM: Artificial
<220> FEATURE:
<223> OTHER INFORMATION: Synthetic peptide

<400> SEQUENCE: 14

Trp Gly Gln Gly Thr Leu Val Thr Val Ser Ala
1               5                   10

<210> SEQ ID NO 15
<211> LENGTH: 219
<212> TYPE: PRT
<213> ORGANISM: Artificial
<220> FEATURE:
<223> OTHER INFORMATION: Synthetic peptide

<400> SEQUENCE: 15

Asp Ile Val Met Thr Gln Ala Thr Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Ile Thr Tyr Leu Tyr Trp Phe Leu Gln Arg Pro Gly Gln Ser
        35                  40                  45

Pro Gln Arg Leu Ile Tyr Tyr Met Ser Asn Leu Ala Ser Gly Val Pro
    50                  55                  60

Asp Arg Phe Ser Gly Arg Gly Ser Gly Thr Asp Phe Thr Leu Arg Ile
65                  70                  75                  80

Ser Arg Val Glu Ala Glu Asp Val Gly Val Tyr Tyr Cys Met Gln Ser
                85                  90                  95

Leu Glu Tyr Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 16
<211> LENGTH: 20
```

```
<212> TYPE: PRT
<213> ORGANISM: Artificial
<220> FEATURE:
<223> OTHER INFORMATION: Synthetic peptide

<400> SEQUENCE: 16

Met Arg Cys Leu Ala Glu Phe Leu Gly Leu Leu Val Leu Trp Ile Pro
1               5                   10                  15

Gly Ala Ile Gly
            20

<210> SEQ ID NO 17
<211> LENGTH: 454
<212> TYPE: PRT
<213> ORGANISM: Artificial
<220> FEATURE:
<223> OTHER INFORMATION: Synthetic peptide

<400> SEQUENCE: 17

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ser Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Glu Asn Tyr Tyr Gly Ser Ser Phe Phe Ala Tyr Trp Gly Gln Gly
            100                 105                 110

Thr Leu Val Thr Val Ser Ala Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Leu Leu
                165                 170                 175

Gln Ser Gly Leu Tyr Thr Leu Ser Ser Ser Val Thr Val Thr Ser Asn
            180                 185                 190

Thr Trp Pro Ser Gln Thr Ile Thr Cys Asn Val Ala His Pro Ala Ser
        195                 200                 205

Ser Thr Lys Val Asp Lys Lys Ile Glu Pro Arg Val Pro Ile Thr Gln
    210                 215                 220

Asn Pro Cys Pro Pro Leu Lys Glu Cys Pro Pro Cys Ala Ala Pro Asp
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Met Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300
```

```
Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Arg Ala Leu Pro
            325                 330                 335

Ser Pro Ile Glu Lys Thr Ile Ser Lys Pro Arg Gly Pro Val Arg Ala
        340                 345                 350

Pro Gln Val Tyr Val Leu Pro Pro Ala Glu Glu Met Thr Lys Lys
    355                 360                 365

Glu Phe Ser Leu Thr Cys Met Ile Thr Gly Phe Leu Pro Ala Glu Ile
370                 375                 380

Ala Val Asp Trp Thr Ser Asn Gly Arg Thr Glu Gln Asn Tyr Lys Asn
385                 390                 395                 400

Thr Ala Thr Val Leu Asp Ser Asp Gly Ser Tyr Phe Met Tyr Ser Lys
                405                 410                 415

Leu Arg Val Gln Lys Ser Thr Trp Glu Arg Gly Ser Leu Phe Ala Cys
            420                 425                 430

Ser Val Val His Glu Gly Leu His Asn His Leu Thr Thr Lys Thr Ile
        435                 440                 445

Ser Arg Ser Leu Gly Lys
    450
```

```
<210> SEQ ID NO 18
<211> LENGTH: 19
<212> TYPE: PRT
<213> ORGANISM: Artificial
<220> FEATURE:
<223> OTHER INFORMATION: Synthetic peptide

<400> SEQUENCE: 18

Met Lys Cys Ser Trp Val Ile Phe Phe Leu Met Ala Val Val Ile Gly
1               5                   10                  15

Val Asn Ser

<210> SEQ ID NO 19
<211> LENGTH: 717
<212> TYPE: DNA
<213> ORGANISM: Artificial
<220> FEATURE:
<223> OTHER INFORMATION: Synthetic oligonucleotide

<400> SEQUENCE: 19
atgaggtgcc tagctgagtt cctggggctg cttgtgctct ggatccctgg agccattggg      60
gatattgtga tgactcaggc tacaccctct gtacctgtca ctcctggaga gtcagtatcc     120
atctcctgca ggtctagtaa gagtcttctg catagtaatg gcatcactta cttgtattgg     180
ttcctgcaga ggccaggcca gtctcctcag cgcctgatat attatatgtc caaccttgcc     240
tcaggagtcc cagacaggtt cagtggcaga gggtcaggaa ctgatttcac actgagaatc     300
agtagagtgg aggctgagga tgtgggtgtt tattactgta tgcaaagtct agaatatccg     360
tacacgttcg gaggggggac caagctggaa ataaaacggg ctgatgctgc accaactgta     420
tccatcttcc caccatccag tgagcagtta acatctggag gtgcctcagt cgtgtgcttc     480
ttgaacaact ctaccccaa agacatcaat gtcaagtgga agattgatgg cagtgaacga     540
caaaatggcg tcctgaacag ttggactgat caggacagca agacagcac ctacagcatg     600 agcagcaccc tcacgttgac caaggacgag tatgaacgca taacagcta tcctgtgag     660 gccactcaca agacatcaac ttcacccatt gtcaagagct caacaggaa tgagtgt       717
```

```
<210> SEQ ID NO 20
<211> LENGTH: 717
<212> TYPE: DNA
<213> ORGANISM: Artificial
<220> FEATURE:
<223> OTHER INFORMATION: Synthetic oligonucleotide

<400> SEQUENCE: 20
atgaggtgcc tagctgagtt cctggggctg cttgtgctct ggatccctgg agccattggg      60
gatattgtga tgactcaggc tacaccctct gtacctgtca ctcctggaga gtcagtatcc     120
atctcctgca ggtctagtaa gagtcttctg catagtaatg gcatcactta cttgtattgg     180
ttcctgcaga ggccaggcca gtctcctcag cgcctgatat attatatgtc aaccttgcc     240 tcaggagtcc cagacaggtt cagtggcaga gggtcaggaa ctgatttcac actgagaatc     300
agtagagtgg aggctgagga tgtgggtgtt tattactgta tgcaaagtct agaatatccg     360
tacacgttcg gaggggggac caagctggaa ataaaacggg ctgatgctgc accaactgta     420
tccatcttcc caccatccag tgagcagtta acatctggag gtgcctcagt cgtgtgcttc     480
ttgaacaact ctaccccaa agacatcaat gtcaagtgga agattgatgg cagtgaacga     540
caaaatggcg tcctgaacag ttggactgat caggacagca agacagcac ctacagcatg     600 agcagcaccc tcacgttgac caaggacgag tatgaacgac ataacagcta cctgtgag     660 gccactcaca agacatcaac ttcacccatt gtcaagagct caacaggaa tgagtgt      717

<210> SEQ ID NO 21
<211> LENGTH: 32
<212> TYPE: DNA
<213> ORGANISM: Artificial
<220> FEATURE:
<223> OTHER INFORMATION: Synthetic oligonucleotide

<400> SEQUENCE: 21
gatcgaattc accccgcctc caggggggccc ag                                    32

<210> SEQ ID NO 22
<211> LENGTH: 32
<212> TYPE: DNA
<213> ORGANISM: Artificial
<220> FEATURE:
<223> OTHER INFORMATION: Synthetic oligonucleotide

<400> SEQUENCE: 22
gatcgaattc gccgcagtcc ttgccggtga ag                                     32

<210> SEQ ID NO 23
<211> LENGTH: 30
<212> TYPE: DNA
<213> ORGANISM: Artificial
<220> FEATURE:
<223> OTHER INFORMATION: Synthetic oligonucleotide

<400> SEQUENCE: 23
gatcgaattc aaatgctttg atgagacccg                                        30

<210> SEQ ID NO 24
<211> LENGTH: 29
<212> TYPE: DNA
<213> ORGANISM: Artificial
<220> FEATURE:
<223> OTHER INFORMATION: Synthetic oligonucleotide
```

<400> SEQUENCE: 24
gatcgaattc gccttcgcac caggtccgg          29

<210> SEQ ID NO 25
<211> LENGTH: 31
<212> TYPE: DNA
<213> ORGANISM: Artificial
<220> FEATURE:
<223> OTHER INFORMATION: Synthetic oligonucleotide

<400> SEQUENCE: 25
gatcgaattc catacagctt gtctgagcag c          31

<210> SEQ ID NO 26
<211> LENGTH: 32
<212> TYPE: DNA
<213> ORGANISM: Artificial
<220> FEATURE:
<223> OTHER INFORMATION: Synthetic oligonucleotide

<400> SEQUENCE: 26
gatcgaattc gatgttgcag agccgtccag cg          32

<210> SEQ ID NO 27
<211> LENGTH: 30
<212> TYPE: DNA
<213> ORGANISM: Artificial
<220> FEATURE:
<223> OTHER INFORMATION: Synthetic oligonucleotide

<400> SEQUENCE: 27
gatcgaattc gatgagcgct gcttcttggg          30

<210> SEQ ID NO 28
<211> LENGTH: 29
<212> TYPE: DNA
<213> ORGANISM: Artificial
<220> FEATURE:
<223> OTHER INFORMATION: Synthetic oligonucleotide

<400> SEQUENCE: 28
gatcgaattc gcaggcctcc aggcggcag          29

<210> SEQ ID NO 29
<211> LENGTH: 28
<212> TYPE: DNA
<213> ORGANISM: Artificial
<220> FEATURE:
<223> OTHER INFORMATION: Synthetic oligonucleotide

<400> SEQUENCE: 29
gatcgaattc ctcaccagag tccaactg          28

<210> SEQ ID NO 30
<211> LENGTH: 29
<212> TYPE: DNA
<213> ORGANISM: Artificial
<220> FEATURE:
<223> OTHER INFORMATION: Synthetic oligonucleotide

<400> SEQUENCE: 30
gatcgaattc ggcctggcgc cccggggag          29

<210> SEQ ID NO 31
<211> LENGTH: 35

<210> SEQ ID NO 31
<211> LENGTH: 35
<212> TYPE: DNA
<213> ORGANISM: Artificial
<220> FEATURE:
<223> OTHER INFORMATION: Synthetic oligonucleotide

<400> SEQUENCE: 31
ggggatactg tttggaaccc accccgcctc caggg                         35

<210> SEQ ID NO 32
<211> LENGTH: 35
<212> TYPE: DNA
<213> ORGANISM: Artificial
<220> FEATURE:
<223> OTHER INFORMATION: Synthetic oligonucleotide

<400> SEQUENCE: 32
ccctggaggc ggggtgggtt ccaaacagta tcccc                         35

<210> SEQ ID NO 33
<211> LENGTH: 38
<212> TYPE: DNA
<213> ORGANISM: Artificial
<220> FEATURE:
<223> OTHER INFORMATION: Synthetic oligonucleotide

<400> SEQUENCE: 33
gcaaggactg cggcaccgag aagtgctttg agcctcag                      38

<210> SEQ ID NO 34
<211> LENGTH: 38
<212> TYPE: DNA
<213> ORGANISM: Artificial
<220> FEATURE:
<223> OTHER INFORMATION: Synthetic oligonucleotide

<400> SEQUENCE: 34
ctgaggctca aagcacttct cggtgccgca gtccttgc                      38

<210> SEQ ID NO 35
<211> LENGTH: 36
<212> TYPE: DNA
<213> ORGANISM: Artificial
<220> FEATURE:
<223> OTHER INFORMATION: Synthetic oligonucleotide

<400> SEQUENCE: 35
ggaacccact gccagaaaga gaaatgcttt gatgag                        36

<210> SEQ ID NO 36
<211> LENGTH: 36
<212> TYPE: DNA
<213> ORGANISM: Artificial
<220> FEATURE:
<223> OTHER INFORMATION: Synthetic oligonucleotide

<400> SEQUENCE: 36
ctcatcaaag catttctctt tctggcagtg ggttcc                        36

<210> SEQ ID NO 37
<211> LENGTH: 37
<212> TYPE: DNA
<213> ORGANISM: Artificial
<220> FEATURE:
<223> OTHER INFORMATION: Synthetic oligonucleotide

<400> SEQUENCE: 37

```
ggacctggtg cgaaggcaca gccagccagg cctgccg                              37

<210> SEQ ID NO 38
<211> LENGTH: 37
<212> TYPE: DNA
<213> ORGANISM: Artificial
<220> FEATURE:
<223> OTHER INFORMATION: Synthetic oligonucleotide

<400> SEQUENCE: 38
cggcaggcct ggctggctgt gccttcgcac caggtcc                              37

<210> SEQ ID NO 39
<211> LENGTH: 36
<212> TYPE: DNA
<213> ORGANISM: Artificial
<220> FEATURE:
<223> OTHER INFORMATION: Synthetic oligonucleotide

<400> SEQUENCE: 39
gcccactgcc agcggctaag gcatacagct tgtctg                               36

<210> SEQ ID NO 40
<211> LENGTH: 36
<212> TYPE: DNA
<213> ORGANISM: Artificial
<220> FEATURE:
<223> OTHER INFORMATION: Synthetic oligonucleotide

<400> SEQUENCE: 40
cagacaagct gtatgcctta gccgctggca gtgggc                               36

<210> SEQ ID NO 41
<211> LENGTH: 36
<212> TYPE: DNA
<213> ORGANISM: Artificial
<220> FEATURE:
<223> OTHER INFORMATION: Synthetic oligonucleotide

<400> SEQUENCE: 41
ggctctgcaa catcgaaacc aaggcaagct gctatg                               36

<210> SEQ ID NO 42
<211> LENGTH: 36
<212> TYPE: DNA
<213> ORGANISM: Artificial
<220> FEATURE:
<223> OTHER INFORMATION: Synthetic oligonucleotide

<400> SEQUENCE: 42
catagcagct tgccttggtt tcgatgttgc agagcc                               36

<210> SEQ ID NO 43
<211> LENGTH: 39
<212> TYPE: DNA
<213> ORGANISM: Artificial
<220> FEATURE:
<223> OTHER INFORMATION: Synthetic oligonucleotide

<400> SEQUENCE: 43
gccttctgcg acgtggatac cgtggagcgc tgcttcttg                            39

<210> SEQ ID NO 44
<211> LENGTH: 39
<212> TYPE: DNA
<213> ORGANISM: Artificial
```

```
<220> FEATURE:
<223> OTHER INFORMATION: Synthetic oligonucleotide

<400> SEQUENCE: 44
caagaagcag cgctccacgg tatccacgtc gcagaaggc                    39

<210> SEQ ID NO 45
<211> LENGTH: 37
<212> TYPE: DNA
<213> ORGANISM: Artificial
<220> FEATURE:
<223> OTHER INFORMATION: Synthetic oligonucleotide

<400> SEQUENCE: 45
cgcctggagg cctgcgaaac cccaacccag gcggcgc                      37

<210> SEQ ID NO 46
<211> LENGTH: 37
<212> TYPE: DNA
<213> ORGANISM: Artificial
<220> FEATURE:
<223> OTHER INFORMATION: Synthetic oligonucleotide

<400> SEQUENCE: 46
gcgccgcctg ggttggggtt cgcaggcct ccaggcg                       37

<210> SEQ ID NO 47
<211> LENGTH: 39
<212> TYPE: DNA
<213> ORGANISM: Artificial
<220> FEATURE:
<223> OTHER INFORMATION: Synthetic oligonucleotide

<400> SEQUENCE: 47
gacctggcac agtgccaatc cctcaccaga gtccaactg                    39

<210> SEQ ID NO 48
<211> LENGTH: 39
<212> TYPE: DNA
<213> ORGANISM: Artificial
<220> FEATURE:
<223> OTHER INFORMATION: Synthetic oligonucleotide

<400> SEQUENCE: 48
cagttggact ctggtgaggg attggcactg tgccaggtc                    39

<210> SEQ ID NO 49
<211> LENGTH: 40
<212> TYPE: DNA
<213> ORGANISM: Artificial
<220> FEATURE:
<223> OTHER INFORMATION: Synthetic oligonucleotide

<400> SEQUENCE: 49
ccggggcgcc aggcctgtgg ccagcggctc gcaagagtc                    40

<210> SEQ ID NO 50
<211> LENGTH: 40
<212> TYPE: DNA
<213> ORGANISM: Artificial
<220> FEATURE:
<223> OTHER INFORMATION: Synthetic oligonucleotide

<400> SEQUENCE: 50
gactcttgcg gagccgctgg ccacaggcct ggcgccccgg                   40
```

UNITED STATES PATENT AND TRADEMARK OFFICE
CERTIFICATE OF CORRECTION

PATENT NO. : 9,574,013 B2
APPLICATION NO. : 14/649972
DATED : February 21, 2017
INVENTOR(S) : Andras Gruber et al.

Page 1 of 1

It is certified that error appears in the above-identified patent and that said Letters Patent is hereby corrected as shown below:

In the Specification

In Column 1, Lines 17-23, please delete the paragraph and insert:
--This invention was made with government support under Grant Nos. AI088937, HL058837, HL081326, and NS077600, awarded by the National Institutes of Health. The government has certain rights in the invention.-- therefor.

Signed and Sealed this
Twenty-sixth Day of September, 2023

Katherine Kelly Vidal
*Director of the United States Patent and Trademark Office*